United States Patent
Kwong et al.

(10) Patent No.: US 12,338,483 B2
(45) Date of Patent: Jun. 24, 2025

(54) COMPOSITIONS AND METHODS FOR LOGIC-GATED PROFILING OF BIOLOGIC ACTIVITY

(71) Applicant: Georgia Tech Research Corporation, Atlanta, GA (US)

(72) Inventors: Gabriel Kwong, Atlanta, GA (US); Anirudh Sivakumar, Atlanta, GA (US); Quoc Mac, Atlanta, GA (US); Brandon Holt, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 705 days.

(21) Appl. No.: 16/859,881

(22) Filed: Apr. 27, 2020

(65) Prior Publication Data

US 2020/0299749 A1    Sep. 24, 2020

Related U.S. Application Data

(60) Provisional application No. 62/811,619, filed on Feb. 28, 2019.

(51) Int. Cl.
*C12Q 1/37* (2006.01)
*G01N 33/58* (2006.01)

(52) U.S. Cl.
CPC ............. *C12Q 1/37* (2013.01); *G01N 33/582* (2013.01); *G01N 33/587* (2013.01); *G01N 2333/9506* (2013.01); *G01N 2333/96436* (2013.01); *G01N 2333/96486* (2013.01); *G01N 2333/974* (2013.01)

(58) Field of Classification Search
None
See application file for complete search history.

(56) References Cited

U.S. PATENT DOCUMENTS

| | | | |
|---|---|---|---|
| 5,013,556 A | 5/1991 | Woodle et al. | |
| 6,592,847 B1 | 7/2003 | Weissleder et al. | |
| 7,179,655 B2 | 2/2007 | Patricelli | |
| 7,329,506 B2 | 2/2008 | Ward et al. | |
| 7,833,728 B2 | 11/2010 | Pastorek et al. | |
| 8,551,727 B2 | 10/2013 | Kwon et al. | |
| 8,673,267 B2 | 3/2014 | Bhatia et al. | |
| 9,999,687 B2 | 6/2018 | Rajopadhye et al. | |
| 10,006,916 B2 | 6/2018 | Kwong et al. | |
| 2004/0091943 A1 | 5/2004 | Schneider | |
| 2005/0191680 A1 | 9/2005 | Bruno et al. | |
| 2010/0124757 A1 | 5/2010 | Kwon et al. | |
| 2010/0131432 A1 | 5/2010 | Kennedy et al. | |
| 2010/0240050 A1 | 9/2010 | Bhatia et al. | |
| 2011/0189680 A1 | 8/2011 | Keown et al. | |
| 2011/0244483 A1 | 10/2011 | Leeming et al. | |
| 2011/0256567 A1* | 10/2011 | Berthelot ................ C12Q 1/37 435/23 |
| 2013/0017223 A1 | 1/2013 | Hope et al. | |
| 2013/0116405 A1 | 5/2013 | Yu et al. | |
| 2014/0242612 A1 | 8/2014 | Wang et al. | |
| 2015/0018517 A1 | 1/2015 | Rajopadhye et al. | |
| 2015/0065420 A1 | 3/2015 | Soliman et al. | |
| 2015/0132230 A1 | 5/2015 | Bossmann et al. | |
| 2015/0132785 A1 | 5/2015 | Bossmann et al. | |
| 2015/0133752 A1 | 5/2015 | Iverson et al. | |
| 2016/0206726 A1 | 7/2016 | Cobbold et al. | |
| 2017/0049904 A1 | 2/2017 | Lin et al. | |
| 2017/0176458 A1 | 6/2017 | Veidal et al. | |
| 2017/0369843 A1 | 12/2017 | Kahvejian et al. | |
| 2018/0023114 A1 | 1/2018 | Morin et al. | |
| 2018/0085466 A1 | 3/2018 | Bradley et al. | |
| 2018/0335429 A1 | 11/2018 | Bhatia et al. | |
| 2019/0375796 A1 | 12/2019 | Touti et al. | |

FOREIGN PATENT DOCUMENTS

| | | |
|---|---|---|
| KR | 20150129908 A | 11/2015 |
| WO | 0214867 A2 | 2/2002 |
| WO | 2004/005348 A1 | 1/2004 |
| WO | 2008/018933 A2 | 2/2008 |
| WO | 2008/127019 A1 | 10/2008 |
| WO | 2009/111470 A2 | 9/2009 |
| WO | 2010/101628 A2 | 9/2010 |
| WO | 2012/125808 A1 | 9/2012 |
| WO | 2014/079802 A2 | 5/2014 |
| WO | 2014/197816 A1 | 12/2014 |
| WO | 2014/197840 A1 | 12/2014 |
| WO | 2015/148622 A1 | 10/2015 |
| WO | 2015/154006 A1 | 10/2015 |
| WO | 2017/177115 A1 | 10/2017 |
| WO | 2017/180587 A2 | 10/2017 |
| WO | 2017/193070 A1 | 11/2017 |
| WO | 2018/064383 A1 | 4/2018 |
| WO | 2018/068135 A1 | 4/2018 |

OTHER PUBLICATIONS

Abudayyeh, 2012, Nanoparticle-chaperoned urinary "synthetic biomarkers" for profiling proteases in cancer, MIT Thesis.
Arias, 2017, The Untold Story of Grazymes in Oncoimmunology: Novel Opportunities with Old Acquaintances, Trends Cancer, 3(6):407-422.
Aungier, 2016, The extracellular matrix: a new dimension in disease diagnosis and treatment, Biochemist 38(4): 10-15.
Bonnans, 2014, Remodelling the extracellular matrix in development and disease, Nat Rev Mol cell Biol 15(12):786-801.
Cyll, 2017, Tumour heterogeneity poses a significant challenge to cancer biomarker research, British Journal of Cancer, 117(3):367-375.
Deshpande, 2013, Current trends in the use of liposomes for tumor targeting, Nanomed 8(9):1509-28.
Dudani, 2018, Harnessing Protease Activity to Improve Cancer Care, Ann Rev of Cancer Biolog, 2:353-76.
Dudani, 2015, Photoactivated spatiotemporally responsive nanosensors of in vivo protease activity, ACS Nano 9(12):11708-11717.
Dudani, 2016, Sustained-release synthetic biomarkers for monitoring thrombosis and inflammation using point-of-care compatible readouts, Adv Funct Mat 10.1002:1-10.

(Continued)

*Primary Examiner* — Marsha Tsay
(74) *Attorney, Agent, or Firm* — Meunier Carlin & Curfman LLC

(57) ABSTRACT

The disclosure provides methods and compositions to digitally profile biological activity by detecting the activity of at least two biomarkers using protease activity sensors or biocomparators.

13 Claims, 17 Drawing Sheets

Specification includes a Sequence Listing.

(56) References Cited

OTHER PUBLICATIONS

Dudani, 2018, Classification of prostate cancer using a protease activity nanosensor library, PNAS 115(36):8954-8959.
Dudani, 2018, Harnessing protease activity to improve cancer care, Ann Rev Cell Biol 2:353-76.
Egeblad, 2002, New Functions for the Matrix Metalloproteinases in Cancer Progression, Nai Rev Cancer, 2(3):161-174.
Friedman, 2013, The smart targeting of nanoparticles, Curr Pharm Des 19(35):6315-6329.
Galati, 2003, Increased Resistnace of Peptides to Serum Proteases by Modification of their Amino Groups, Z. Naturforsch., 58c, 558-561.
Gang, 2018, Cyclic Peptides: Promising Scaffolds for Biopharmaceuticals, Genes 9:557.
Gootenberg, 2017, Nucleic acid detection with CRISPR-Cas13a/C2c2, Science 356(6336):438-442.
Gootenberg, 2018, Multiplexed and portable nucleic acid detection platform with Cas13, Cas12a, and Csm6, Science, 360(6387):439-444.
Gural, 2018, Engineered livers for infection diseases, Cell Mol Gastroent Hepat 5(2):131-144.
Harris, 2008, Protease-triggered unveiling of bioactive nanoparticles, Small 4(9):1307-1312.
Holt, 2018, Nanosensors to cetect protease activity in vivo for noninvasive diagnostics, J Vis Exp 137:e57937.
Hori, 2011, Mathematical Model Identifies Blood Biomarker-Based Early Cancer Detection Strategies and Limitations, Sci Transl Med, 3(109):109ra116.
Hughes, 2017, Dissecting the role of the extracellular matrix in heart disease, Vet Sci 4(24):1-28.
International Seach Report and Written Opinion issued in International Application No. PCT/US2020/30132, date of mailing: Oct. 22, 2020, 37 pages.
International Search Report and Written Opinion issued in International Application No. PCT/US2020/015828, date of mailing: Jun. 8, 2020, 8 pages.
International Search Report and Written Opinion issued in International Application No. PCT/US2020/15823, date of mailing: Apr. 28, 2020, 10 pages.
International Search Report and Written Opinion mailed Oct. 24, 2019, for PCT/US2019/036039, filed Jun. 7, 2019 (11 pages).
International Search Report and Written Opinion mailed Sep. 4, 2019, for PCT/US19/36155, filed Jun. 7, 2019 (8 pages).
International Search Report and Written Opinion mailed Sep. 12, 2019, for PCT/US2019/036036, filed Jun. 7, 2019 (9 pages).
International Search Report and Written Opinion mailed Sep. 19, 2019, for PCT/US2019/036041, filed Jun. 7, 2019 (8 pages).
Kappelhoff, 2017, Overview of transcriptomic analysis of all human proteases, non-proteolytic homologs and inhibitors, BBA Mol Cell Res 1864:2210-2219.
Kircher, 2004, A dual fluorochrome probe for imaging proteases, Bioconjugate Chem 15:242-248.
Klingler, 2012, Profiling protease activities with dynamic proteomics workflows, Proteomics 12(4-5):587-596.
Kristensen, 2016, Cell-penetrating peptides as tools to enhance non-injectable delivery of biopharmaceuticals, Tissue Barriers 4(2):e1178369.
Kulkarni, 2016, Reporter nanoparticle that monitors its anticancer efficacy in real time, PNAS Early Edition (10 pages).
Kutlu, 2018, Molecular pathogenesis of nonalcoholic steatohepatitis (NASH) related hepatocellular carcinoma, Can J Gast Hepat 2018:8543763 (10 pages).
Kwon, 2017, Ultrasensitive tumor-penetrating nanosensors of protease activity, Nat Biomed Eng 1: art0054 (10 pages).
Kwong, 2013, Mass-encoded synthetic biomarkers for multiplexed urinary monitoring of disease, Nat Biotech 31(1):63-70.
Kwong, 2015, Mathemetical framework for activity-based cancer biomarkers, PNAS 112(41):12627-12632.
Larimer, 2017, Granzyme B PET Imaging as a Predictive Biomarker of Immunotherapy Response, Cancer Res, 77(9):2318-2327.
Lau, 2018, Therapeutic peptides: Historical perspectives, current development trends, and future directions, Bioorganic & Med Chem 26:2700-2707.
Lee, 2018, Implementation of a multiplex and quantitative proteomics platform for assessin protein lysates using DNA-barcoded antibodies, Mol Cell Proteomics 17(6):1245-1258.
Lin, 2009, PEG Hydrogels for the controlled release of biomolecules in regenerative medicine, Pharma Res 26(3):631-643.
Lin, 2013, Nanoparticles that sense thrombin activity as synthetic urinary biomarkers of thrombosis, ACS nano 7(10):9001-9009.
Lin, 2013, The biodegradation of biodegradable polymeric biomaterials, Chapter II.4.3 in Biomaterials Science 3d Ed., Ratner et al., Eds Academic Press 716-728.
Lo, 2018, iRGD-guided tumor-penetrating nanocomplexes for therapeutic siRNA delivery to pancreatic cancer, Mol Cancer Ther 17(11):2377-2388.
Luther, 2018, Hepatic connexin 32 associates with nonalcoholic fatty liver disease severity, Hepatol Comm 2(7):786-797.
Mallinckrodt, 2003, Assessing and interpreting treatment effects in longitudinal clinical trials with missing data, Biol Psychiatry 53:754-760.
Mason, 2011, Proteolytic Networks in Cancer, Trends Cell Biol., 21(4):228-237.
Milletti, 2012, Cell-penetrating peptides: classes, origin, and current landscape, Drug Disc Today 17:850-860.
Nagrath, 2007, Isolation of rare circulating tumour cells in cancer patients by microchip technology, Nature, 450(7173):1235-1239.
Nguyen, 2011, The prototype HIV-1 maturation inhibitor, bevirimat, binds to the CA-SP1 cleavage site in immature Gag particles, Retrovirology 8:101 (13 pages).
Rääägel, 2010, Peptide-mediated protein delivery-which pathways are penetrable?, Biochim Biophys Acta., 1798(12):2240-2248.
Sanchez-Martin, 2017, Selection strategies for anti-cancer antibody discovery: searching off the beaten path, Trends Biotechnol., May 2015, 33(5):292-301.
Schuerle, 2016, Magnetically actuated protease sensors for in vivo tumor profiling, Nano Lett 16:6303-6310.
Sjöblom, 2006, The consensus coding sequences of human breast and colorectal cancers. Science, 314(5797):268-274.
Song, 2012, PROSPER: An integrated feature-based tool for predicting protease substrate cleavage sites, PLOSOne 7(11):e50300 (23 pages).
Tascilar, 1999, Role of tumor markers and mutations in cells and pancreatic juice in the diagnosis of pancreatic cancer, Ann Onc 10(Suppl 4):s107-s110.
Tockman, 1992, Consideratoins in bringing a cancer biomarker to clinical application, Canc Res 52:2711s-2718s.
Van Lehn, 2011, Penetration of lipid bilayers by nanoparticles with environmentally-responsive surfaces, Soft Matter 7:11392-11404.
Voskoboink, 2015, Perforin and granzymes: funtion, dysfunction and human pathology, Nature Reviews Immunol, 15(6):388-400.
Warren, 2014, Disease detection by ultrasensitive quantification of microdosed synthetic urinary biomarkers, JACS 136:13709-13714.
Warren, 2014, Point-of-care diagnostics for noncommunicable diseases using synthetic urinary biomarkers and paper microfluidics, PNAS 111(10):3671-3676.
Buss et al.: Protease activity sensors noninvasively classify bacterial infections and antibiotic responses. eBioMedicine 38:248-256 (2018). https://doi.org/10.1016/j.ebiom.2018.11.031.
Holt et al: Proteases as Biological Bits for Programmable Medicine. bioRxiv (2019). doi:https://doi.org/10.1101/607895.

\* cited by examiner

SEQUENCE LISTING

```
<160> NUMBER OF SEQ ID NOS: 2

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES
<222> LOCATION: (14)..(14)
<223> OTHER INFORMATION: D-Phe

<400> SEQUENCE: 1

Lys Cys Gly Ile Glu Phe Asp Ser Gly Gly Lys Gly Gly Phe Pro Arg
1               5                   10                  15

Ser Gly Gly Gly Cys Lys
            20

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES
<222> LOCATION: (11)..(11)
<223> OTHER INFORMATION: D-Gly
```

```
<400> SEQUENCE: 2

Cys Gly Ile Glu Phe Asp Ser Gly Gly Lys Gly Ala Pro Ala Ala Leu
1               5                   10                  15

Arg Ala Ala Gly Gly Cys Lys
            20
```

COMPOSITIONS AND METHODS FOR LOGIC-GATED PROFILING OF BIOLOGIC ACTIVITY

This application claims priority to U.S. Provisional Application No. 62/811,619, filed on Feb. 28, 2019, which is incorporated herein by reference in its entirety.

STATEMENT OF GOVERNMENT SUPPORT

This invention was made with government support under grant No. DP2HD091793 awarded by the National Institutes of Health. The government has certain rights in the invention.

REFERENCE TO A SEQUENCE LISTING

This application contains a Sequence Listing in computer readable form. The computer readable form is incorporated herein by reference. Said ASCII copy, created on Jun. 23, 2023, is named 61226-703_201_SL.txt and is 1,127 bytes in size.

TECHNICAL FIELD

The disclosure relates to tools, compositions, and methods to digitally profile biological activity.

BACKGROUND

Advances in human health are predicated on increasing the ability to extract meaningful information from complex biological states and using this information to guide diagnosis, prognosis or therapeutic interventions. Currently clinical decisions rely on obtaining information from complex biological states by interrogating "analog" signals, such as biomarker levels, which are prone to noise, imprecision, and heterogeneity. Applying principles from computing to biological systems can improve accuracy and sensitivity in obtaining information from complex biological states, which leads accurate disease diagnoses and increased medical treatment efficacy. For example, computing uses "digital" signals that carry information robustly and are resistant to uncontrolled variables. Using compositions and methods enabling biologic activity to be profiled under a digital framework, such as Boolean logic, can drastically improve the ability to extract meaningful information from complex biological states.

The enzymatic activity of certain proteases has been shown to be of paramount import in monitoring and diagnosing certain pathologies and treatments. More than 550 proteases are encoded by the human genome, and the dysregulation of protease signaling networks is fundamental to the biology of numerous pathologies, including cancer, fibrosis, hematological, and immune disorders (Mason and Joyce, *Trends Cell Biol.*, 21 (4): 228-237 (2011)). Consequently, detection of protease activity can provide meaningful information from complex biological states and prove useful for diagnosis, prognosis, and development of therapeutic treatments. This is especially true of cancers, for which proteases a key role in directing tumorigenesis.

Accurate detection of protease activity can also provide information pertaining to efficacy and specificity of a particular therapeutic treatment. An important and emerging class of therapeutic treatments is immunotherapy. Immunotherapies harness the immune system to treat myriad diseases such as cancer, organ transplant rejection, infectious disease, allergic disease, autoimmunity and chronic inflammation. These therapies employ both the humoral and cellular arms of the immune response using therapeutic antibodies, cytokines, and cell-based therapies. Despite the broad potential of immunotherapies, many patients fail to see clinical benefit, while others can develop immunotherapy resistance. Patients who respond to immunotherapy often exhibit unconventional response patterns that can be misinterpreted as disease progression. Due to inadequacies in technologies for response monitoring and for identifying underlying resistance mechanisms, not only do diseases persist in the population, but drug development and clinical trials face significant obstacles. To realize the full benefits of immunotherapy, improved methods for monitoring biomarkers during immunotherapy, including protease activity, is required.

Prior methods of measuring protease activity, such as structural biology, enzymology, and inhibitor-based assays, have provided crucial information regarding proteases. However, these techniques often lack sensitivity and fail to distinguish between various disease states or off-target activity.

In the context of diagnostics, tissue biopsy remains the gold standard diagnostic but is invasive and samples less the 0.1% of the total disease site (Cyll et al., *Br J Cancer,* 117 (3): 367-375 (2017)). Liquid biopsies offer a noninvasive approach, but biomarker dilution in blood significantly limits sensitivity (Nagrath, S., et al, *Nature,* 450 (7173): 1235-1239 (2007); Hori, et al., *Sci Transl Med,* 3 (109): 109ra16 (2011)). Imaging techniques can also be limited by low sensitivity and specificity, as well as the unconventional response patterns commonly associated with immunotherapy that can result in misidentification of responding patients as cases of treatment failure. The development of better, non-invasive biomarkers will identify responsive patients sooner and illuminate mechanisms of new immunotherapies.

Therefore, it is an object of the invention to provide biologic activity sensors that leverage protease biology for specific and sensitive, noninvasive diagnostics.

SUMMARY

The disclosure provides methods and compositions to digitally profile biological activity by detecting the activity of at least two biomarkers. The biomarkers may be proteins or enzymes, including proteases and/or cytolytic proteins. The methods and compositions detect the activity of biomarkers using a digital framework. To establish a digital framework, the disclosure provides logic-gated biomarker activity sensors. The activity sensors use AND-gated logic to probe the activity of two biomarkers. The activity sensors sense biological activity by a specific biomarker as a bit. Activity of one biomarker represents state "1", and lack of activity represents the state "0". The activity of two biomarkers represents state "1,1" and provides a TRUE output. The activity of only one of two biomarkers represents state "1,0" and no biomarker activity represents state "0,0". States "0,1" and "0,0" both provide a FALSE output.

The activity sensors may comprise protease substrates designed to sense biological activity by a specific protease cleavage event as a biological bit, where, uncleaved substrates represent state "0" and cleaved substrates represent state "1". The sensors use AND-gated logic to probe the activity of two proteases simultaneously by providing a TRUE output only after cleavage events by both proteases. Cleavage of one or none of the protease substrates provides a FALSE output. Using this concept, the disclosure provides methods and compositions using logic-gated activity sensors that leverage protease activity provides, for example, specific and sensitive, noninvasive diagnostics.

The disclosure provides methods and compositions for determining protease activity in a biological sample using a protease activity sensor. The protease activity sensor comprises a first protease substrate and a second protease substrate. Each substrate is cleaved by a different protease, for example, a first protease and a second protease. The sensor may employ AND-gated logic. Thus, when both substrates are cleaved, the protease activity sensor provides a detectable signal (a TRUE output), indicating the activity of both the first and second protease in the sample. However, if only one, or none, of the substrates is cleaved, no detectable sample is produced (a FALSE output).

The protease sensor may be conjugated to a reporter molecule, such as a fluorescent molecule, to provide the detectable signal. Where the reporter molecule is a fluorescent molecule, the first and second protease substrates may be conjugated to a fluorescent quencher. Cleaving the protease substrates removes the quencher, which allows the fluorescent molecule to provide the detectable signal (a TRUE output). However, if one or both protease substrates are not cleaved, the fluorescent quencher is not removed and prevents the detectable signal (a FALSE output).

The protease sensor may be a cyclic peptide. The cyclic peptide may comprise two distinct protease substrates. The substrates may separate a fluorescent reporting molecule and a quencher.

The protease sensor may be conjugated to a scaffold, such as a nanoparticle. A plurality of protease sensors may be conjugated to a scaffold. Conjugating protease sensors to a scaffold increases their valency of presentation, increases the rate of proteolysis, and thereby amplifies the detectable signal. This can improve signal-to-noise, especially when the protease sensor is delivered in vivo.

The disclosure provides methods and compositions for determining biomarker activity in a biological sample using a bicomparator. The bicomparator may comprise a reporting molecule encased in a liposome. The liposome is contained within a peptide cage. Cleavage of the peptide cage by a protease releases the liposome. The liposome can be perforated by a cytolytic protein, such as perforin, thereby releasing the reporter molecule. The bicomparator may employ AND-gated logic. Upon release, the reporter molecule provides a detectable signal (a TRUE output), which indicates the activity of both the protease and cytolytic protein in the sample. Without a protease capable of cleaving the peptide cage and cytolytic protein to perforate the liposome, the reporter molecule is not released and no detectable signal is produced (a FALSE output). The reporter molecule may be a fluorescent molecule.

Bicomparators may be conjugated to a scaffold, such as a nanoparticle. A plurality of biocomparators may be conjugated to a scaffold. Conjugating a plurality of bicomparators to a scaffold increases their valency of presentation, increases the rate of proteolysis, and thereby amplifies the detectable signal. This can improve signal-to-noise, especially when the bicomparators are delivered in vivo.

The protease substrates, including the peptide cage of the bicomparator, are designed to be cleaved by specific proteases. This allows the presence of a particular protease in a sample to be determined. The presence or absence of a particular protease may be indicative of a protease dysregulation. A protease dysregulation may indicate the presence of a diseased state, such as cancer, fibrosis, a hematological disorder, an immune disorder, a viral infection, or a bacterial infection. Thus, the methods and compositions of the disclosure can be used to diagnose a disease or disease progression.

Protease activity may be indicative of an immune response to immunotherapy or therapeutic drugs. Thus, the methods and compositions of the disclosure can be used to monitor immunotherapies and therapeutic drug treatments. Monitoring can include measuring the efficacy, specificity, and response of specific treatments. This ability of the disclosed methods and compositions is especially useful for cancer immunotherapies.

Monitoring an immune response may include detecting the activity of one or more proteases and/or cytolytic protein. The activity of the one or more proteases and/or cytolytic protein may be promoted by a therapeutic agent. In this way, the activity, specificity, and or efficacy of a therapeutic agent may be monitored.

Cancer immunotherapies are limited by their off-target effects. Methods of noninvasively detecting intratumoral immune activity substantially improve treatment monitoring. Solely monitoring immune activity in a patient may not confirm immunotherapy efficacy because, for example, the immune system is activated against another pathology (e.g., a viral infection). The specificity provided by the AND-gated logic protease activity sensors and bicomparators allows, for example, immune activity in tumors to be distinguished from immune activity caused by viral infections. The methods and compositions of the disclosure allow for monitoring of intratumoral immune activity and can distinguish between immune activity caused by a tumor, therapeutic treatment, and another pathology, such as a viral infection.

The methods and compositions of the disclosure may be used in vitro or in vivo. The methods of the disclosure can include administering to a subject an amount of the protease sensors or bicomparators as described herein. The methods may include monitoring the activity of one or more proteases and/or cytolytic proteins in the subject. The activity of the proteases and/or cytolytic proteins may indicate a protease dysregulation and/or immune response in the subject. The protease dysregulation may indicate the presence of a diseased state in the subject. The diseased state may be cancer, fibrosis, a hematological disorder, an immune disorder, a viral infection, or a bacterial infection. The activity of the proteases and/or the activity cytolytic protein may be promoted by a therapeutic agent. The methods may include monitoring the activity of at least one of granzyme B (GzmB), thrombin (Thrb), a metalloproteinase (MMP), or a viral protease.

DETAILED DESCRIPTION

Figure 1:
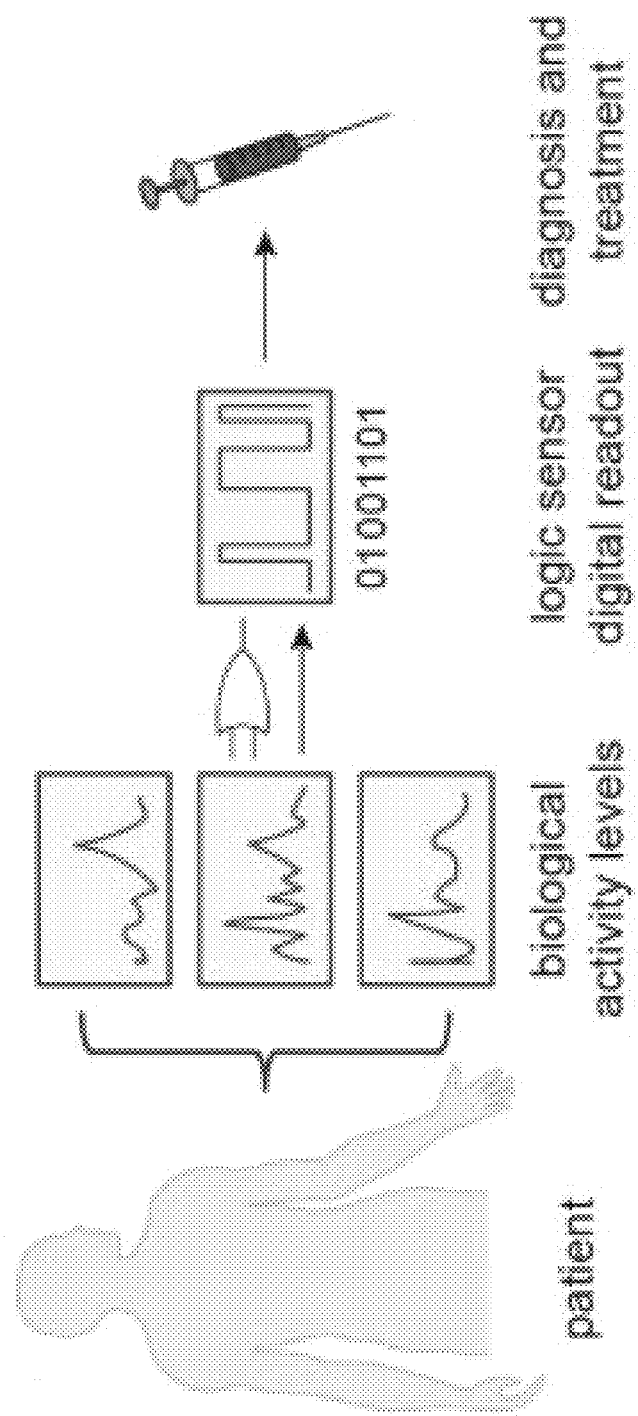
FIG. 1 shows the principle behind digitally reading biological activity.

The disclosure provides methods and compositions to digitally profile biological activity by detecting the activity of at least two biomarkers. The biomarkers can include proteins or enzymes, including proteases and/or cytolytic proteins. The methods and compositions detect the activity of biomarkers using a digital framework. To establish a digital framework, the disclosure provides logic-gated biomarker activity sensors. The methods and compositions use AND-gated logic to probe the activity of two biomarkers. The methods and compositions sense biological activity by a specific biomarker as a bit. Activity of one biomarker represents state "1", and lack of activity represents the state "0". The activity of two biomarkers represents state "1,1" and provides a TRUE output. The activity of only one of two biomarkers represents state "1,0" and no biomarker activity represents state "0,0". States "0,1" and "0,0" both provide a FALSE output. Since the methods and compositions require the activity of two specific biomarkers they can provide a digital profile of biologic activity with assurance.

Enzymes are differentially expressed under different physiological states of interest, such as in response to a disease, infection, immune response, or therapeutic treatment. For example, dysregulated protease activity may be indicative of a disease state. Dysregulated proteases have important consequences in the progression of diseases, including cancers, in that they may alter cell signaling, help drive cancer proliferation, invasion, angiogenesis, avoidance of apoptosis, and metastasis. However, the activity of a single enzyme, including a protease, is often dispositive of a biological response. By detecting the activity of multiple enzymes, such as proteases and cytolytic proteins, a response can be more confidently determined and reported using a binary signal, such as a TRUE or FALSE output.

The methods and compositions are useful in monitoring and diagnosing diseases, immune responses, and therapeutic activity. Monitoring may include longitudinal monitoring, including, for example, disease state changes, immune activity, and/or response to therapeutic activity. The methods and compositions are useful for longitudinal monitoring and personalized medicine as well as for recruitment, enrichment, qualification, and stratification of study participants. The methods and compositions are useful for detecting efficacy of treatment, monitoring response to treatment over time, and detecting relapse and remission. Detection of reporters in a sample from the subject may indicate presence of a disease, stage of a disease, and a rate or a level of disease activity in the subject. Tests using compositions of the disclosure can be administered and read non-invasively, quickly, and without imaging by x-rays or other modalities.

Compositions of the disclosure may be used to determine subject responsiveness to a drug and efficacy of treatment. For instance, the compositions can be administered and tested at multiple time points and read to observe trends over time in disease changes or progression or remission. Regardless of whether a subject has received a treatment or the compositions are being used diagnostically, the compositions may be used to measure activity within the body. As such, the invention provides an additional understanding of the disease instead of merely the effect of the disease. Compositions may be used to study the disease and/or to study other associated activity. For example, the activity or progression of the disease may be detected, such as growth rate of a tumor. For subjects receiving drug treatment, the composition may be used to detect activity indicative of whether the participant is responding to the treatment. For example, activity sensors may be designed to detect whether a tumor is growing or shrinking in size, the rate of activity or progression of the disease, whether a particular dosage of the drug is effective, and whether a participant is likely to respond to treatment.

The methods and compositions can be used to detect the activity of two specific biomarkers to digitally profile whether a subject responds to multiple treatments. By measuring the activity of two specific biomarkers, the methods and compositions of the disclosure allows the type of response in a subject to be more accurately determined, allowing for the use of a binary signal. For example, certain drugs may be used to treat a disease. However, the drugs may be directed to different methods of treating the disease. When treating a disease like nonalcoholic steatohepatitis (NASH), one drug may be an anti-fibrotic drug and another drug may be an anti-inflammation or anti-NASH drug. Detecting activity of both drugs by interrogating the activity of a biomarker associated with each drug invoked in the body of a participant provides insight as to why a participant did or did not respond to treatment.

Additionally, the methods and compositions may be used to detect whether the subject is about to respond to treatment. For example, a subject may have a tumor that has been treated or is being treated with a checkpoint blockade drug. The subject may appear to be unresponsive to treatment because the tumor continues to grow in size after administering the checkpoint blockade. However, because the invention detects biologic activity of two biomarkers within the body, the invention may detect that the growth is from an influx of immune cells. Simultaneously, due to the specificity afforded by the methods and compositions of the disclosure, it can be distinguished whether the immune response is caused by the checkpoint blockade drug or a pathology, such as a viral infection. Thus, it is determined that the subject is about to respond to the treatment, rather than unresponsive.

The methods and compositions of the disclosure may include protease activity sensors. Such activity sensors can include a variety of reporter molecules that are detectable in a sample, but are only detectable upon contact and cleavage from two proteases associated with localized immune responses or cancer progression. Cleavage by only one protease will not result in a state represented by "1,1", and will thus provide a FALSE output. Cleavage by both proteases will result in a state represented by "1,1", and will thus provide a TRUE output. The protease sensors may be provided to a subject in vivo, and the reporter molecules detectable in a body fluid upon protease cleavage that releases the reporter molecules.

As shown in FIG. 1A, the protease activity sensors of the subject disclosure allow for biologic activity to be provided in a digital readout. As described herein, the protease activity sensors can provide non-invasive reporting of the activity of two proteases through engineering of two protease-specific cleavage sites on the sensor. For example, the protease-specific substrates (e.g., cleavage sites) may be cleaved by a protease(s) that are promoted by caner or immune activity.

Figure 2:
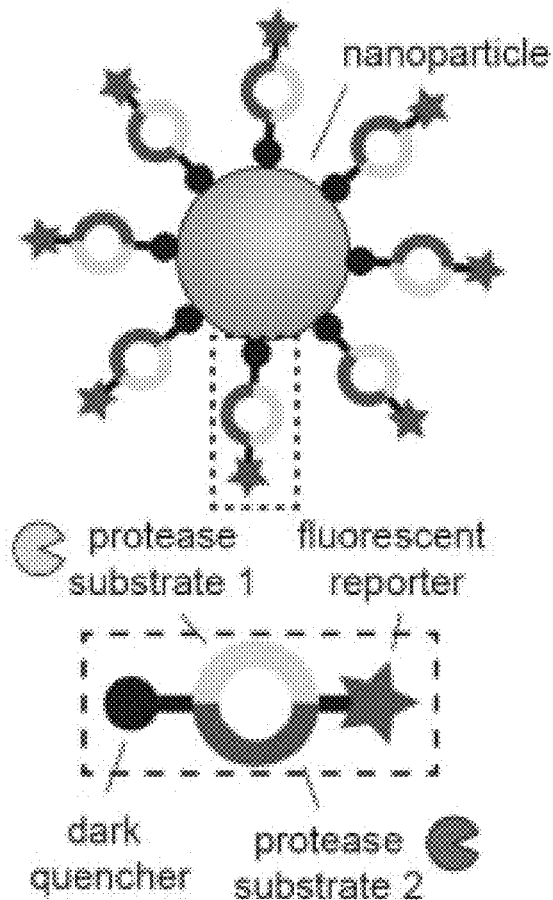
FIG. 2 shows a schematic of example of protease activity sensors.

FIG. 2 provides a non-limiting schematic of a protease activity sensor. As shown in FIG. 2, a plurality of protease activity sensors may be attached to a scaffold, such as a nanoparticle. The protease activity sensors each have a reporter molecule, shown as a star in FIG. 2. The reporter molecule may be a fluorescent molecule. The reporter molecule is attached to two different protease substrates, which are cleaved by the activity of two different proteases. As shown in FIG. 2, when the reporter molecule is a fluorescent molecule, the protease activity sensor may comprise a fluorescent quencher, shown as a black circle in FIG. 2. The fluorescent quencher prevents the fluorescent molecule from providing a detectable signal. Upon cleavage of the two different proteases, the reporter molecule is released. As show in FIG. 2, release may permit the reporter molecule to distance from the fluorescent quencher, thereby permitting a detectable signal.

Figure 3:
FIG. 3 shows the principle behind AND-gated logic in protease activity sensors.

FIG. 3 shows how the protease activity sensors provide AND-gated logic to probe the activity of two proteases simultaneously by providing a TRUE output only after cleavage events by both proteases. A signal of "0,0" results from no protease cleavage, and provides a FALSE output. A signal of "0,1" results from protease cleavage by only one protease, and provides a FALSE output. A signal of "1,1" results from protease cleavage by both proteases, and provides a TRUE output.

The methods and compositions of the disclosure may include bicomparators. The bicomparators may comprise a variety of reporter molecules. The reporter molecules are encased in a liposome. The liposome is contained within a peptide cage, which is a substrate for a particular protease(s). Cleavage of the peptide cage by a protease releases the liposome. The liposome can be perforated by a cytolytic protein, such as perforin. The reporting molecules are only detected upon cleavage of the peptide cage by a protease and perforation of the liposome by a cytolytic protein. Release of the reporter molecule will result in a state represented by "1,1", and will thus provide a TRUE output. The bicomparators may be provided to a subject in vivo, and the reporter molecules detectable in a body fluid upon release of the reporter molecules.

Figure 4:
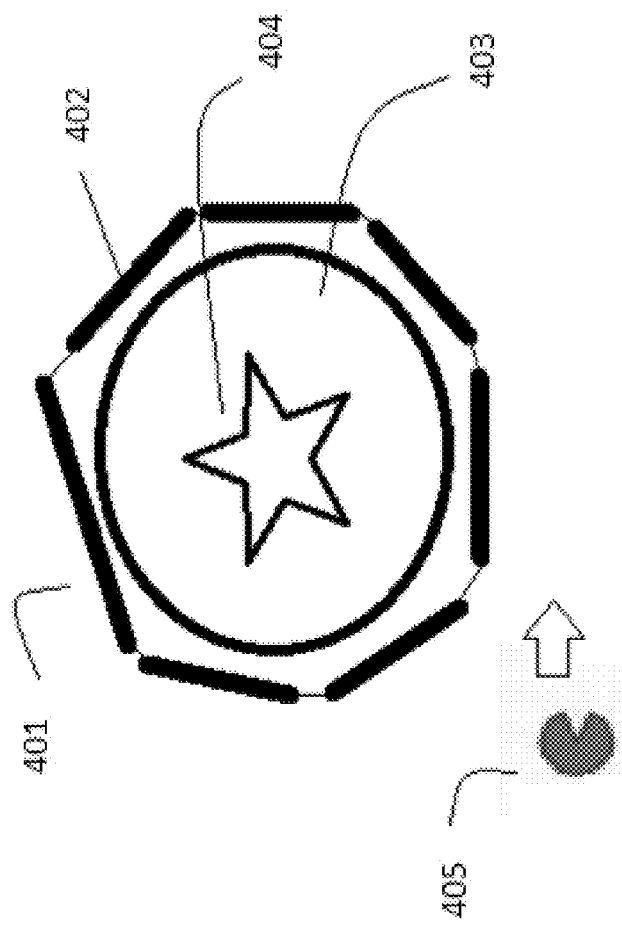
FIG. 4 shows a schematic for an AND-gated biocomparator.
Figure 5:
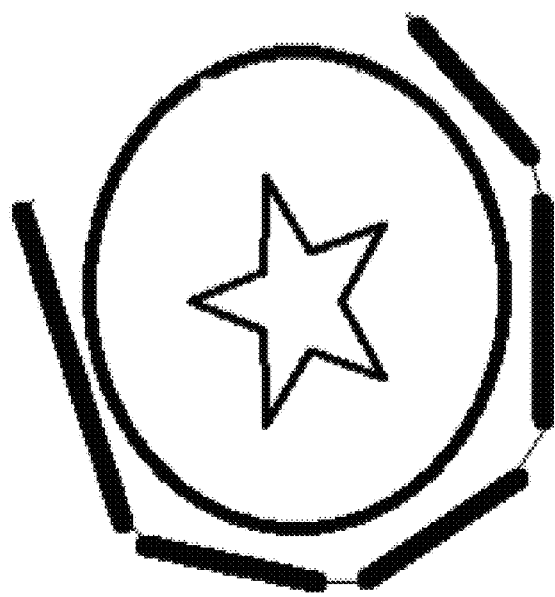
FIG. 5 shows a schematic of a biocomparator with a cleaved peptide cage.
Figure 6:
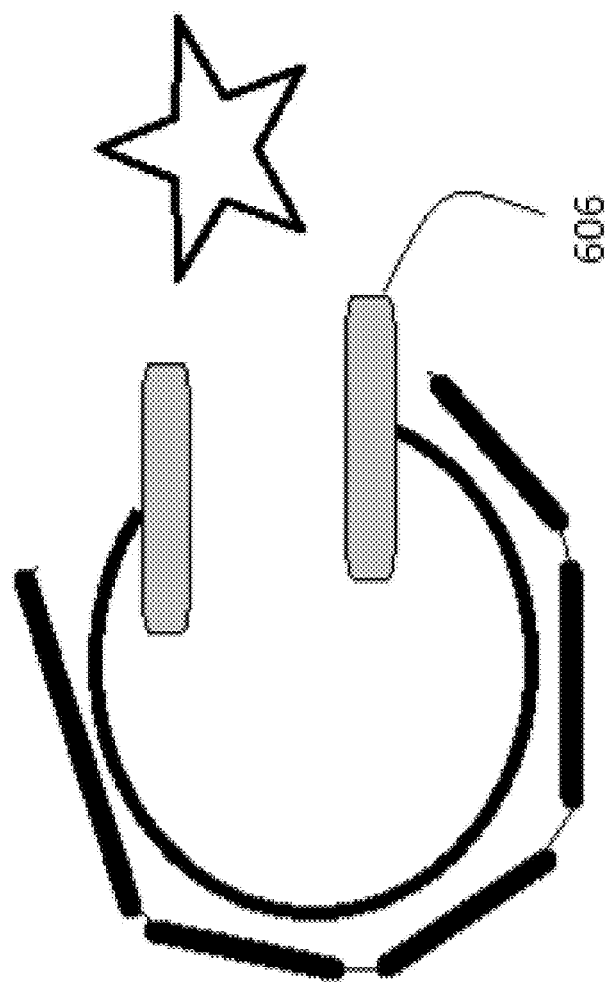
FIG. 6 shows a schematic of a biocomparator with a perforated liposome and released reporter molecule.

FIGS. 4-6 provides a non-limiting schematic of a bicomparator. As shown in FIG. 4, the bicomparator 401 has reporter molecule 404, shown as a star. The reporter molecule may be a fluorescent molecule. The reporter molecule 404 is encased within a liposome 403. The liposome 403 is contained within a peptide cage 402. A protease 405, contacts the bicomparator 401. As shown in FIG. 5, the protease cleaves the peptide cage. Then, as shown in FIG. 6, a cytolytic protein 606, such as perforin, perforates the liposome and releases the reporter molecule, thereby providing a detectable signal.

Figure 7:
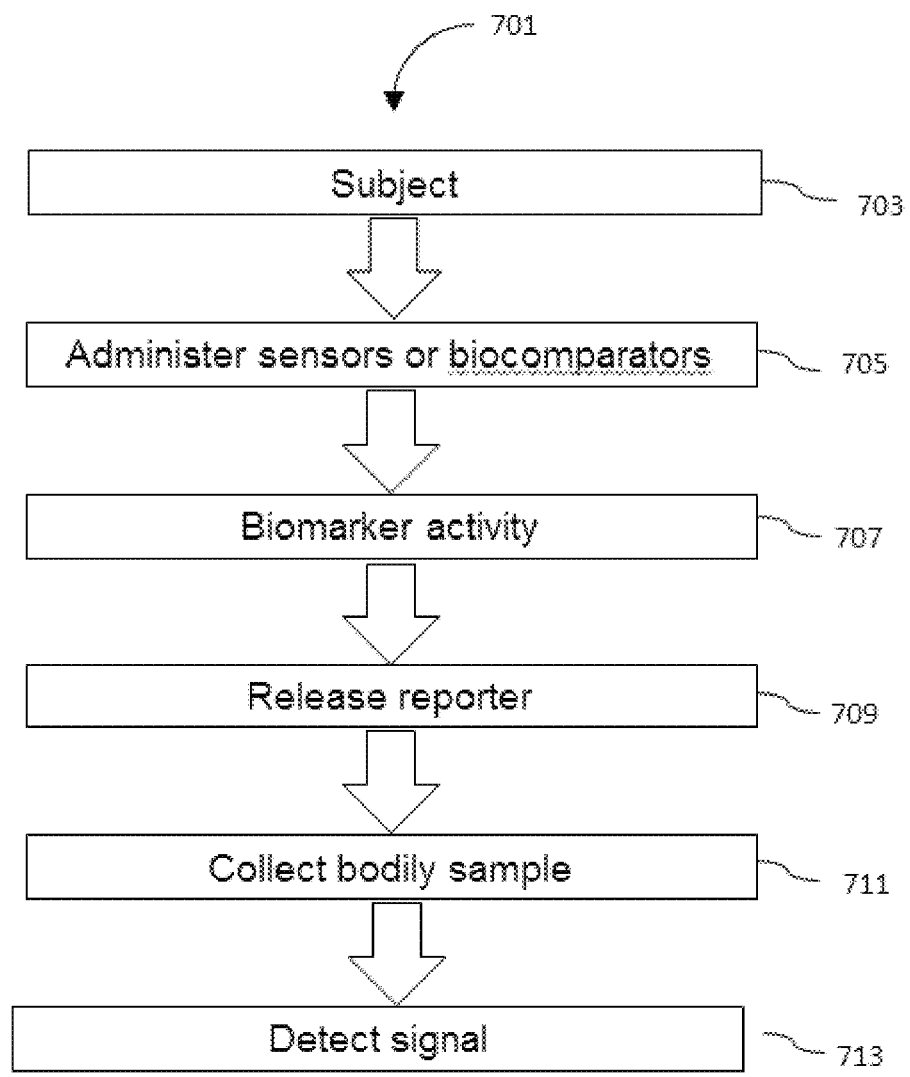
FIG. 7 shows an exemplary method of the disclosure.

The disclosure includes methods in which the protease activity sensors or bicomparators of the disclosure are administered to a subject in vivo to monitor or diagnose a disease or treatment efficacy. FIG. 7 shows a non-limiting example of such a method 701. The method 701 may be implemented in the context of a longitudinal study to determine efficacy of therapeutic treatment. A subject 705 is included who will receive, or is receiving a treatment. The protease activity sensors or bicomparators are administered 705 to the subject. The method 701 may include monitoring change in disease condition in a subject who has received the therapeutic treatment for the disease by making measurements at multiple points over time (i.e., in a longitudinal manner). Two specific biomarkers contact the protease activity sensors or bicomparators, which act upon the protease activity sensors or bicomparators 707. This causes the protease activity sensors or bicomparators to release the reporter molecule 709. A sample is obtained 711 from the subject, and an assay is performed to detect the signal in the sample 713. By detecting the reporters in a sample from the subject, the activity, and thus presence, of the two biomarkers in the sample is identified. The presence and activity of the two biomarkers in the sample may indicate a progression in disease state or immune response promoted by the therapeutic treatment.

The method 701 may be used to detect disease-associated activity within the body such that activity of the two biomarkers detected using the sensors shows disease progression or that treatment is being effective. The protease activity sensors or bicomparators may be given over time to monitor a subject's response to treatment and to show whether or not the treatment is effectively treating the disease in the subject. Different drugs or combinations of drugs can be studied in different subjects or at different times to identify drugs or combinations that work well for treating a condition. The protease activity sensors or bicomparators provide a marker of health/disease progression and provide the marker very quickly (detecting a signal in a sample from the subject may be within hours of administering the protease activity sensors or bicomparators). The protease activity sensors or bicomparators can specifically report the activity of multiple enzymes including ones for which expression is dysregulated in the disease state and others that are specific to co-morbidities. Preferably, the enzymes (e.g., extracellular proteases) have an expression that is upregulated due to a certain pathology, treatment, or condition.

The method 701 may be used for monitoring cancer progression in a subject. The subject may be suspected of having cancer, known to have cancer (active or in remission), at risk of developing cancer, and/or undergoing treatment for cancer including immuno-oncological (I-O) therapies. A protease sensor may be administered 705 to the subject. The sensor may include a reporter linked by two protease substrates. The protease substrates are each sensitive to a protease for which the activity is indicative of a characteristic in the tumor environment (e.g., enzymes upregulated in expanding tumors or tumors in regression, or enzymes indicative of active or inhibited immune responses).

Similarly, a biocomparator may be administered 705 to the subject. The biocomparator may have a peptide cage that is a substrate for a protease, for which the activity is indicative of a characteristic in the tumor environment. The liposome of the biocomparator may be perforated by a protein for which activity is indicative of a characteristic in the tumor environment.

As discussed herein, depending on the protease activity the activity sensors are engineered to report on and the patient's disease and treatment status, information garnered from reporter levels in patient samples can be used to diagnose and/or stage the disease, monitor progression, predict responsiveness to a given therapy, and monitor therapeutic effectiveness including differentiating between anti-tumor immune response, general immune response, and tumor progression. Activity sensors can be administered by any suitable method. The activity sensors may be delivered intravenously or aerosolized and delivered to the lungs, for example, via a nebulizer. In other examples, the activity sensors may be administered to a subject transdermally, intradermally, intraarterially, intralesionally, intratumorally, intracranially, intraarticularly, intratumorally, intramuscularly, subcutaneously, orally, topically, locally, inhalation, injection, infusion, or by other method or any combination known in the art.

Proteases are a class of enzymes that includes over 550 members encoded within the human genome, many of which have disease specific roles, including critical roles in immunity. For example, cytotoxic T-cell mediated target cell killing is a protease-driven process involving: 1) death receptor signaling and caspase activation, proteases whose activity mediates cell death, and 2) secretion of granzymes, proteases that enter target cells through a perforin dependent mechanism to activate caspase-mediated cell death. Moreover, proteases are central to other aspects of immune activity including cell migration, matrix degradation and repair, and complement activation, while tumor proteases such as inflammatory and matrix degrading proteases are established hallmarks of cancer (Arias, et al., *Trends Cancer*, 3 (6): 407-422 (2017); Egeblad, et al., *Nai Rev Cancer*, 2 (3): 161-174 (2002)).

Proteases provide an innovative approach for immunotherapy response monitoring given that proteases play a central role in the underlying biology of immunity, oncology, and the pathophysiology of multiple diseases (Dudani, et al., *Ann Rev of Cancer Biology*, (2018)). For example, the mark of a "hot" tumor is signified by an effective immune infiltrate of cytotoxic T cells that kill cancer cells primarily through a perforin-dependent, granzyme-mediated pathway, the latter of which comprise a family of potent serine proteases (Larimer, et al., *Cancer Res*, 77 (9): 2318-2327 (2017); Voskoboinik, et al., *Nat Rev Immunol*, 15 (6): 388-400 (2015)). Tumor expression of proteases, including inflammatory and matrix degrading proteases, is well established as a hallmark of fundamental tumor biology including angiogenesis, growth, and metastasis (Dudani, et al., *Ann Rev of Cancer Biology*, (2018)). These protease signatures can be used to stage cancer, monitor progression and regression, and provide early indication of drug response. The activity of immune and disease site specific proteases early in treatment to allows identification of activity biomarkers that predict treatment efficacy and indicate resistance to immunotherapy.

In one embodiment, proteases amplify detection signals at the disease or therapeutic site (×1000 fold). Following protease cleavage, the reporter molecules are concentrated into urine, instead of being diluted in blood, further enriching the signal up to 100-fold. This enables, for example, ultrasensitive and early detection of T-cell activity that precedes radiographic detectable changes at the disease site.

Protease substrates contain a recognition sequence for the protease to cleave. Cleavage of the protease substrates may release a reporter molecule linked to the substrates. The protease substrates may each be a substrate for a particular protease known to be associated with a diseased cell. Proteases known to be associated with diseased cells or tissues include but are not limited to serine proteases, cysteine proteases, aspartate proteases, threonine proteases, glutamic acid proteases, metalloproteases, asparagine peptide lyases, serum proteases, cathepsins, Cathepsin B, Cathepsin C, Cathepsin D, Cathepsin E, Cathepsin K, Cathepsin L, kallikreins, hK1, hK10, hK15, plasmin, collagenase, Type IV collagenase, stromelysin, Factor Xa, chymotrypsin-like protease, trypsin-like protease, elastase-like protease, subtilisin-like protease, actinidain, bromelain, calpain, caspases, caspase-3, Mirl-CP, papain, HIV-1 protease, HSV protease, CMV protease, chymosin, renin, pepsin, matriptase, legumain, plasmepsin, nepenthesin, metalloexopeptidases, metalloendopeptidases, matrix metalloproteases (MMP), MMP1, MMP2, MMP3, MMP8, MMP9, MMP13, MMP11, MMP14, urokinase plasminogen activator (uPA), enterokinase, prostate-specific antigen (PSA, hK3), interleukin-10 converting enzyme, thrombin, FAP (FAP-a), dipeptidyl peptidase, meprins, granzymes and dipeptidyl peptidase IV (DPPIV/CD26).

The protease substrates may be tumor-specific protease substrates. Exemplary tumor associated proteases include but are not limited to cathepsin B, cathepsin D, cathepsin E, cathepsin K, cathepsin L, kallikrein 1, kallikrein 3 (PSA), kallikrein 10, kallikrein15, uPA, uPAR, caspases, matrix metalloproteinases such as MMP1, MMP2, MMP8, MMP9, MMP13, MMP14, and ADAM. In another embodiment, the protease substrates are cell-specific protease substrates, such as T-cell specific protease substrates. Exemplary cell-specific proteases include but are not limited to neutrophil serine proteases such as cathepsin G, neutrophil elastase, and proteinase 3, mucosa-associated lymphoid tissue 1 (MALT1), granzymes, and cysteine proteinases of the caspase family, such as caspase-3,-6,-7,-8.

The protease substrates may be substrates specific for proteases associated with inflammation and/or programmed cell death. Several proteases are known to be associated with inflammation and programmed cell death (e.g., including apoptosis, pyroptosis and necroptosis). The activity levels of those proteases are accordingly indicative of immune system activity. Caspases (cysteine-aspartic proteases, cysteine aspartases or cysteine-dependent aspartate-directed proteases) are a family of protease enzymes including a cysteine in their active site that nucleophilically cleaves a target protein only after an aspartic acid residue. Caspase-1, Caspase-4, Caspase-5 and Caspase-11 are associated with inflammation. Serine proteases also function in apoptosis and inflammation and their differential expression is therefore also indicative of an immune response. Immune cells express serine proteases such as granzymes, neutrophil elastase, cathepsin G, proteinase 3, chymase, and tryptase.

The disclosed protease activity sensors and biocomparators may be used to differentiate between programmed cell death indicative of an immune response and necrosis naturally found during tumor progression. In contrast to programmed cell death, where caspases and serine proteases are the primary proteases, calpains and lysosomal proteases (e.g., cathepsins B and D) are the key proteases in necrosis. Accordingly, calpain and cathepsin levels indicated by activity sensor reporter measurements can provide information regarding necrotic cell death to supplement the immuno-oncological information.

The protease activity sensors may release a reporter molecule upon cleavage by two different proteases. The detectable signal may be the cleavage product or peptide fragment of the protease substrate itself. Upon cleavage a fragment of the protease substrate is released into circulation and detected in urine by mass spectrometry. Cleavage by one protease may release the reporter molecule. However, no detectable signal can be detected from the released reporter molecule until cleavage of a second protease. Such a second cleavage may, for example, cleave a fluorescent quencher from the reporter molecule, thereby permitting detection. Alternatively, the detection signal is a protease substrate engineered with a quencher molecule before the cleavage site(s) and a fluorescent reporter after the cleavage site(s). Upon cleavage of the protease substrate, the quencher and fluorescent reporter are separated, with the reporter being released into circulation. The fluorescent signal is detected in the urine by standard methods such as flow cytometry.

The protease substrates can be conjugated to the reporter molecules, quenchers, and/or scaffolds using methods known in the art. In one embodiment, the protease substrate is conjugated through the introduction of a linker that forms a covalent conjugate between the protease substrate and the reporter molecule, quencher, and/or scaffold. Exemplary reactions that can be used to link the protease substrate include but are not limited to amine-to-amine crosslinkers using NHS esters, thiol-to-thiol crosslinkers using maleimides, amine-to-thiol crosslinkers using NHS esters and maleimides, and biotin/streptavidin interactions.

Reporter molecules, released from activity sensors of the invention, may be detected by any suitable detection method able to detect the presence the reporter molecule, directly or indirectly. For example, reporters may be detected via a ligand binding assay, which is a test that involves binding of the capture ligand to an affinity agent. Reporters may be directly detected, following capture, through optical density, radioactive emissions, or non-radiative energy transfers. Alternatively, reporters may be indirectly detected with antibody conjugates, affinity columns, streptavidin-biotin conjugates, PCR analysis, DNA microarray, or fluorescence analysis.

A ligand binding assay often involves a detection step, such as an ELISA, including fluorescent, colorimetric, bioluminescent and chemiluminescent ELISAs, a paper test strip or lateral flow assay, or a bead-based fluorescent assay.

In one example, a paper-based ELISA test may be used to detect the liberated reporter in urine. The paper-based ELISA may be created inexpensively, such as by reflowing wax deposited from a commercial solid ink printer to create an array of test spots on a single piece of paper. When the solid ink is heated to a liquid or semi-liquid state, the printed wax permeates the paper, creating hydrophobic barriers. The space between the hydrophobic barriers may then be used as individual reaction wells. The ELISA assay may be performed by drying the detection antibody on the individual reaction wells, constituting test spots on the paper, followed by blocking and washing steps. Urine from the urine sample taken from the subject may then be added to the test spots, then streptavidin alkaline phosphate (ALP) conjugate may be added to the test spots, as the detection antibody. Bound ALP may then be exposed to a color reacting agent, such as BCIP/NBT (5-bromo-4-chloro-3'-indolyphosphate p-toluidine salt/nitro-blue tetrazolium chloride), which causes a purple colored precipitate, indicating presence of the reporter molecule.

In another example, volatile organic compounds may be detected by analysis platforms such as gas chromatography instrument, a breathalyzer, a mass spectrometer, or use of optical or acoustic sensors.

Gas chromatography may be used to detect compounds that can be vaporized without decomposition (e.g., volatile organic compounds). A gas chromatography instrument includes a mobile phase (or moving phase) that is a carrier gas, for example, an inert gas such as helium or an unreactive gas such as nitrogen, and a stationary phase that is a microscopic layer of liquid or polymer on an inert solid support, inside a piece of glass or metal tubing called a column. The column is coated with the stationary phase and the gaseous compounds analyzed interact with the walls of the column, causing them to elute at different times (i.e., have varying retention times in the column). Compounds may be distinguished by their retention times.

A modified breathalyzer instrument may also be used to detect volatile organic compounds. In a traditional breathalyzer that is used to detect an alcohol level in blood, a subject exhales into the instrument, and any ethanol present in the subject's breath is oxidized to acetic acid at the anode. At the cathode, atmospheric oxygen is reduced. The overall reaction is the oxidation of ethanol to acetic acid and water, which produces an electric current that may be detected and quantified by a microcontroller. A modified breathalyzer instrument exploiting other reactions may be used to detect various volatile organic compounds.

Mass spectrometry may be used to detect and distinguish reporters based on differences in mass. In mass spectrometry, a sample is ionized, for example by bombarding it with electrons. The sample may be solid, liquid, or gas. By ionizing the sample, some of the sample's molecules are broken into charged fragments. These ions may then be separated according to their mass-to-charge ratio. This is often performed by accelerating the ions and subjecting them to an electric or magnetic field, where ions having the same mass-to-charge ratio will undergo the same amount of deflection. When deflected, the ions may be detected by a mechanism capable of detecting charged particles, for example, an electron multiplier. The detected results may be displayed as a spectrum of the relative abundance of detected ions as a function of the mass-to-charge ratio. The molecules in the sample can then be identified by correlating known masses, such as the mass of an entire molecule to the identified masses or through a characteristic fragmentation pattern.

When the reporter includes a nucleic acid, the reporter may be detected by various sequencing methods known in the art, for example, traditional Sanger sequencing methods or by next-generation sequencing (NGS). NGS generally refers to non-Sanger-based high throughput nucleic acid sequencing technologies, in which many (i.e., thousands, millions, or billions) of nucleic acid strands can be sequenced in parallel. Examples of such NGS sequencing includes platforms produced by Illumina (e.g., HiSeq, MiSeq, NextSeq, MiniSeq, and iSeq 100), Pacific Biosciences (e.g., Sequel and RSII), and Ion Torrent by ThermoFisher (e.g., Ion S5, Ion Proton, Ion PGM, and Ion Chef systems). It is understood that any suitable NGS sequencing platform may be used for NGS to detect nucleic acid of the reporter molecule as described herein. Analysis may be performed directly on the biological sample or the reporter molecule may be purified to some degree first. For example, a purification step may involve isolating the reporter molecule from other components in the biological sample. Purification may include methods such as affinity chromatography. The isolated or purified reporter molecule does not need to be 100% pure or even substantially pure prior to analysis.

The reporter molecule may be attached to a label or may itself comprise a label. Labels suitable for use in the reporter molecule include any type of label detectable by standard methods, including spectroscopic, photochemical, biochemical, electrical, optical, or chemical methods. The label may be a fluorescent label. A fluorescent label is a compound including at least one fluorophore. Commercially available fluorescent labels include, for example, fluorescein phosphoramidites, rhodamine, polymethadine dye derivative, phosphores, Texas red, green fluorescent protein, CY3, and CY5. Other known techniques, such as chemiluminescence or colormetrics (enzymatic color reaction), can also be used to detect the reporter. Quencher compositions in which a "donor" fluorophore is joined to an "acceptor" chromophore by a short bridge that is the binding site for the enzyme may also be used. The signal of the donor fluorophore is quenched by the acceptor chromophore through a process believed to involve resonance energy transfer (RET), such as fluorescence resonance energy transfer (FRET). Cleavage of the peptide results in separation of the chromophore and fluorophore, removal of the quench, and generation of a subsequent signal measured from the donor fluorophore. Examples of FRET pairs include 5-Carboxyfluorescein (5-FAM) and CPQ2, FAM and DABCYL, Cy5 and QSY21, Cy3 and QSY7.

The reporter molecule may comprise one or more protease substrates engineered with a quencher molecule before the cleavage site(s) and a fluorophore or fluorescent reporter after the cleavage site(s). Quencher molecules are known in the art. Exemplary quencher molecules include but are not limited to Deep Dark Quenchers (Eurogentec), DABCYL, TAMRA, BHQ-1®, BHQ-2®, BHQ-3®, BBQC)-650, ECLIPSE, Iowa Black® quenchers, and QSY. Exemplary fluorophores or fluorescent reporters include but are not limited to 6-FAMTm, TETTm, JOETM HEXTM, VICO, cyanine 3, ROXTM, LC Red 640, cyanine 5, fluorescein isothiocyanate (FITC), rhodamine (tetramethyl rhodamine isothiocyanate, TRITC, Oregon Green, Pacific Blue, Pacific Green, Pacific Orange, Texas Red, Alexa Fluor 350, Alexa Fluor 405, Alexa Fluor 488, Alexa Fluor 532, Alexa Fluor 546, Alexa Fluor 555, Alexa Fluor 568, Alexa Fluor 594, Alexa Fluor 647, Alexa Fluor 680, and Alexa Fluor 750.

The protease activity sensors or biocomparators may comprise other reporter molecules such as avidin, biotin, beta-galactosidase, luciferase, alkaline phosphatase (AP), and horseradish peroxidase (HRP). The reporter molecule may be cleaved from the protease substrates, and released into circulation. The reporter molecule may be released from a bicomparators, and released into circulation. The reporter molecules are then detected in urine samples using appropriate detection method such as but not limited to ELISA, Western blotting, immunoassays, and bioluminescent assays.

The protease activity sensors or biocomparators may include ligands to aid them in targeting particular tissues or organs. When administered to a subject, the protease activity sensors or biocomparators may be trafficked in the body through various pathways depending on how they enter the body. For example, if administered intravenously, they will enter systemic circulation from the point of injection and may be passively trafficked through the body.

Protease activity sensors or biocomparators can include a scaffold. The scaffold may further comprise a tuning domain or be conjugated to a tuning domain. The tuning domain modifies a distribution or residence time of the protease activity sensors or biocomparators within a subject when administered to the subject. The protease activity sensors or biocomparators may be tuned via the tuning domains in numerous ways to facilitate detecting enzymatic activity within the body in specific cells or in a specific tissue. For example, the protease activity sensors or biocomparators may be tuned to promote distribution to a specific tissue or to improve a residence time in the subject or in the specific tissue. Tuning domains may include, for example, molecules localized in rapidly replicating cells to better target tumor tissue.

When administered to a subject, the protease activity sensors or bicomparators are trafficked through the body and may diffuse from the systemic circulation to a specific tissue, where the reporter may be released via enzymes indicative of cancer progression or immune response. The reporter molecule may then diffuse back into circulation where it may pass renal filtration and be excreted into urine, whereby detection of the reporter molecule in the urine sample indicates enzymatic activity in the target tissue.

The scaffold may be any suitable platform for trafficking the protease activity sensors or biocomparators through the body of a subject. The scaffold may be any material or size suitable to serve as a scaffold or platform. Preferably the scaffold is biocompatible, non-toxic, and non-immunogenic and does not provoke an immune response in the body of the subject to which it is administered. The scaffold may also function as a targeting means to target the protease activity sensors or biocomparators to a tissue, cell or molecule. The scaffold may be a polymer scaffold. The scaffold may, for example, result in passive targeting to tumors or other specific tissues by circulation. Other types of scaffolds include, for example, compounds that facilitate active targeting to tissue, cells or molecules. Examples of scaffolds include, but are not limited to, nanoparticles such as iron oxide or gold nanoparticles, aptamers, peptides, proteins, nucleic acids, polysaccharides, polymers, antibodies or antibody fragments and small molecules. The scaffold may include a variety of materials such as iron, ceramic, metallic, natural polymer materials such as hyaluronic acid, synthetic polymer materials such as poly-glycerol sebacate, and non-polymer materials, or combinations thereof. The scaffold may be composed in whole or in part of polymers or non-polymer materials, such as alumina, calcium carbonate, calcium sulfate, calcium phosphosilicate, sodium phosphate, calcium aluminate, and silicates. Polymers include, but are not limited to: polyamides, polycarbonates, polyalkylenes, polyalkylene glycols, polyalkylene oxides, cellulose ethers, cellulose esters, nitro celluloses, polymers of acrylic and methacrylic esters, methyl cellulose, ethyl cellulose, and hydroxypropyl cellulose. Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, poly-anhydrides, polyurethanes, and natural polymers such as alginate and other polysaccharides including dextran and cellulose, collagen, albumin and other proteins, copolymers and mixtures thereof. In general, these biodegradable polymers degrade either by enzymatic hydrolysis or exposure to water in vivo, by surface or bulk erosion. These biodegradable polymers may be used alone, as physical mixtures (blends), or as co-polymers. In preferred embodiments, the scaffold includes biodegradable polymers so that whether the reporter is cleaved from the scaffold, the scaffold will be degraded in the body. By providing a biodegradable scaffold, accumulation and any associated immune response or unintended effects of intact activity sensors remaining in the body may be minimized.

Other biocompatible polymers include PEG, PVA and PVP, which are all commercially available. PVP is a non ionogenic, hydrophilic polymer having a mean molecular weight ranging from approximately 10,000 to 700,000 and has the chemical formula $(C_6H_9NO)[n]$. PVP is also known as poly [1 (2 oxo 1 pyrrolidinyl)ethylene]. PVP is nontoxic, highly hygroscopic and readily dissolves in water or organic solvents.

Polyvinyl alcohol (PVA) is a polymer prepared from polyvinyl acetates by replacement of the acetate groups with hydroxyl groups and has the chemical formula (CH2CHOH) [n]. Most polyvinyl alcohols are soluble in water.

Polyethylene glycol (PEG), also known as poly(oxyethylene) glycol, is a condensation polymer of ethylene oxide and water. PEG refers to a compound that includes repeating ethylene glycol units. The structure of PEG may be expressed as H—(O—CH2-CH2)n-OH. PEG is a hydrophilic compound that is biologically inert (i.e., non-immunogenic) and generally considered safe for administration to humans.

When PEG is linked to a particle, it provides advantageous properties, such as improved solubility, increased circulating life, stability, protection from proteolytic degradation, reduced cellular uptake by macrophages, and a lack of immunogenicity and antigenicity. PEG is also highly flexible and provides bio-conjugation and surface treatment of a particle without steric hindrance. PEG may be used for chemical modification of biologically active compounds, such as peptides, proteins, antibody fragments, aptamers, enzymes, and small molecules to tailor molecular properties of the compounds to particular applications. Moreover, PEG molecules may be functionalized by the chemical addition of various functional groups to the ends of the PEG molecule, for example, amine-reactive PEG (BS (PEG) n) or sulfhydryl-reactive PEG (BM (PEG) n).

The scaffold may be a biocompatible scaffold, such as a scaffold including polyethylene glycol (PEG). The biocompatible scaffold may include multiple subunits of covalently linked polyethylene glycol maleimide (PEG-MAL), for example, an 8-arm PEG-MAL scaffold. A PEG-containing scaffold may be selected because it is biocompatible, inexpensive, easily obtained commercially, has minimal uptake by the reticuloendothelial system (RES), and exhibits many advantageous behaviors. For example, PEG scaffolds inhibit cellular uptake of particles by numerous cell types, such as macrophages, which facilitates proper distribution to a specific tissues and increases residence time in the tissue.

An 8-arm PEG-MAL is a type of multi-arm PEG derivative that has maleimide groups at each terminal end of its eight arms, which are connected to a hexaglycerol core. The maleimide group selectively reacts with free thiol, SH, sulfhydryl, or mercapto group via Michael addition to form a stable carbon sulfur bond. Each arm of the 8-arm PEG-MAL scaffold may be conjugated to peptides, for example, via maleimide-thiol coupling or amide bonds.

The PEG-MAL scaffold may be of various sizes, for example, a 10 kDa scaffold, a 20 kDa scaffold, a 40 kDa scaffold, or a greater than 40 kDa scaffold. The hydrodynamic diameter of the PEG scaffold in phosphate buffered saline (PBS) may be determined by various methods known in the art, for example, by dynamic light scattering. Using such techniques, the hydrodynamic diameter of a 40 kDa PEG-MAL scaffold was measured to be approximately 8 nm. In preferred embodiments, a 40 kDa PEG-MAL scaffold is provided as the scaffold when the protease activity sensors or bicomparators are administered subcutaneously because the scaffold readily diffuses into systemic circulation but is not readily cleared by the reticuloendothelial system.

The size of the PEG-MAL scaffold affects the distribution and residence time of the protease activity sensors or bicomparators in the body because particles smaller than about 5 nm in diameter are efficiently cleared through renal filtration of the body, even without proteolytic cleavage. Further, particles larger than about 10 nm in diameter often drain into lymphatic vessels. In one example, where a 40 kDa 8-arm PEG-MAL scaffold was administered intravenously, the scaffold was not renally cleared into urine.

The protease activity sensors or biocomparators may include cyclic peptides that are structurally resistant to non-specific proteolysis and degradation in the body. Cyclic peptides can include protease-specific substrates or pH-sensitive bonds that allow the otherwise non-reactive cyclic peptide to release a reactive reporter molecule in response to the presence of the enzymes discussed herein. Cyclic peptides can require cleavage at a plurality of cleavage sites to increase specificity. The plurality of sites can be specific for the different proteases. Polycyclic peptides can be used comprising 2, 3, 4, or more cyclic peptide structures with various combinations of enzymes or environmental conditions required to linearize or release the functional peptide or other molecule. Cyclic peptides can include depsipeptides wherein hydrolysis of one or more ester bonds releases the linearized peptide. Such peptides can be used to tune the timing of peptide release in environments such as plasma.

Figure 8:
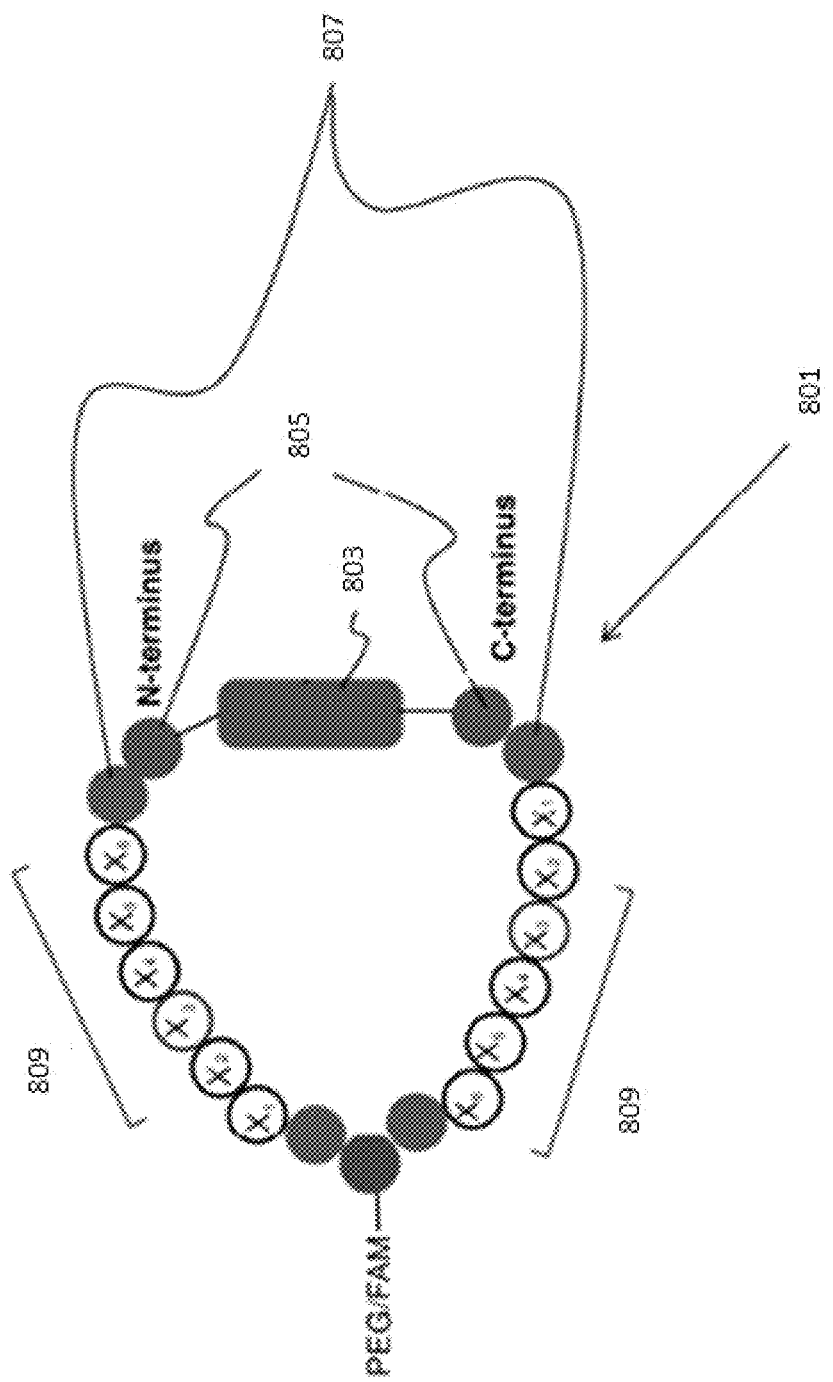
FIG. 8 shows an exemplary cyclic protein activity sensor.

FIG. 8 shows an exemplary protease activity sensor comprising cyclic peptide 801 having a protease-specific substrates 809 and a stable cyclization linker 803. The protease-specific substrates 809 are each cleaved by a different protease and may comprise any number of amino acids in any order. For example, X1 may be glycine. X2 may be serine. X3 may be aspartic acid. X4 may be phenylalanine. X5 may be glutamic acid. X6 may be isoleucine. These amino acids may differ between individual substrates in order to be specific to different proteases. The N-terminus and C-terminus, coupled to the cyclization linker 803 comprise cyclization residues 805. The peptide may be engineered to address considerations such as protease stability, steric hindrance around cleavage site, macrocycle structure, and rigidity/flexibility of peptide chain. The type and number of spacer residues 807 can be chosen to address and alter many of those properties by changing the spacing between the various functional sites of the cyclic peptide. The cyclization linker and the positioning and choice of cyclization residues can also impact the considerations discussed above. Tuning domains such as PEG, reporters such as FAM, and quenchers can be included in the cyclic peptide.

Tuning domains may include ligands to aid it targeting particular tissues or organs. When administered to a subject, the protease activity sensors or biocomparators are trafficked in the body through various pathways depending on how they enters the body.

Cell surface receptors are membrane-anchored proteins that bind ligands on the outside surface of the cell. In one example, the ligand may bind ligand-gated ion channels, which are ion channels that open in response to the binding of a ligand. The ligand-gated ion channel spans the cell's membrane and has a hydrophilic channel in the middle. In response to a ligand binding to the extracellular region of the channel, the protein's structure changes in such a way that certain particles or ions may pass through. By providing tuning domains that include ligands for proteins present on the cell surface, the protease activity sensors or biocomparators have a greater opportunity to reach and enter specific cells to detect enzymatic activity within those cells.

By providing tuning domains, distribution of the protease activity sensors or biocomparators may be modified because ligands may target specific cells or specific tissues in a subject via binding of the ligand to cell surface proteins on the targeted cells. The ligands of tuning domains may be selected from a group including a small molecule; a peptide; an antibody; a fragment of an antibody; a nucleic acid; and an aptamer. Ligands may also promote accumulation of the protease activity sensors or biocomparators in a specific tissue type.

When the protease activity sensors or biocomparators are administered to a subject, they may be recognized as a foreign substance by the immune system and subjected to immune clearance, thereby never reaching the specific cells or specific tissue where the specific enzymatic activity can release the reporter molecule. Furthermore, generation of an immune response can defeat the purpose of immune-response-sensitive activity monitoring. To inhibit immune detection, it is preferable to use a biocompatible scaffold so that it does not elicit an immune response, for example, a biocompatible scaffold may include one or more subunits of polyethylene glycol maleimide. Further, the molecular weight of the polyethylene glycol maleimide scaffold may be modified to facilitate trafficking within the body and to prevent clearance by the reticuloendothelial system. Through such modifications, the distribution and residence time in the body or in specific tissues may be improved.

In various embodiments, the protease activity sensors or biocomparators may be engineered to promote diffusion across a cell membrane. Hydrophobic chains may also be provided as tuning domains to facilitate diffusion across a cell membrane.

The tuning domains may include any suitable hydrophobic chains that facilitate diffusion, for example, fatty acid chains including neutral, saturated, (poly/mono) unsaturated fats and oils (monoglycerides, diglycerides, triglycerides), phospholipids, sterols (steroid alcohols), zoosterols (cholesterol), waxes, and fat-soluble vitamins (vitamins A, D, E, and K).

The tuning domains may include cell-penetrating peptides. Cell-penetrating peptides (CPPs) are short peptides that facilitate cellular intake/uptake. CPPs preferably have an amino acid composition that either contains a high relative abundance of positively charged amino acids such as lysine or arginine or has sequences that contain an alternating pattern of polar/charged amino acids and nonpolar, hydrophobic amino acids. See Milletti, 2012, Cell-penetrating peptides: classes, origin, and current landscape, *Drug Discov Today* 17:850-860, incorporated by reference. Suitable CPPs include those known in the literature as Tat, R6, R8, R9, Penetratin, pVEc, RRL helix, Shuffle, and Penetramax. See Kristensen, 2016, Cell-penetrating peptides as tools to enhance non-injectable delivery of biopharmaceuticals, *Tissue Barriers* 4 (2): e1178369, incorporated by reference.

Protease activity sensors or biocomparators may include a biocompatible polymer as a tuning domain to shield the activity sensor from immune detection or inhibit cellular uptake of the activity sensor by macrophages.

When a foreign substance is recognized as an antigen, an antibody response may be triggered by the immune system. Generally, antibodies will then attach to the foreign substance, forming antigen-antibody complexes, which are then ingested by macrophages and other phagocytic cells to clear those foreign substances from the body. As such, when an protease activity sensors or biocomparators enter the body, they may be recognized as an antigen and subjected to immune clearance, preventing them from reaching a specific tissue to detect biomarker activity. To inhibit immune detection, for example, PEG tuning domains may be linked to the activity sensor. PEG acts as a shield, inhibiting recognition as a foreign substance by the immune system. By inhibiting immune detection, the tuning domains improve the residence time in the body or in a specific tissue.

Enzymes have a high specificity for specific substrates by binding pockets with complementary shape, charge and hydrophilic/hydrophobic characteristic of the substrates. As such, enzymes can distinguish between very similar substrate molecules to be chemoselective (i.e., preferring an outcome of a chemical reaction over an alternative reaction), regioselective (i.e., preferring one direction of chemical bond making or breaking over all other possible directions), and stereo specific (i.e., only reacting on one or a subset of stereoisomers). Steric effects are nonbonding interactions that influence the shape (i.e., conformation) and reactivity of ions and molecules, which results in steric hindrance. Steric hindrance is the slowing of chemical reactions due to steric bulk, affecting intermolecular reactions. Various groups of a molecule may be modified to control the steric hindrance among the groups, for example to control selectivity, such as for inhibiting undesired side-reactions. By providing the protease activity sensors or biocomparators with tuning domains such as spacer residues between the scaffold and the cleavage site and/or any bioconjugation residue, steric hindrance among components may be minimized to increase accessibility of the cleavage site(s) to specific proteases.

Alternatively, steric hindrance can be used as described above to prevent access to the cleavage site(s) until an unstable cyclization linker (e.g., an ester bond of a cyclic depsipeptide) has degraded. Such unstable cyclization linkers can be other known chemical moieties that hydrolyze in defined conditions (e.g., pH or presence of a certain analyte) which may be selected to respond to specific characteristics of a target environment.

Protease activity sensors or biocomparators may include D-amino acids aside from the protease cleavage site(s) to further prevent non-specific protease activity. Other non-natural amino acids may be incorporated into the peptides, including synthetic non-native amino acids, substituted amino acids, or one or more D-amino acids.

In some embodiments, tuning domains may include synthetic polymers such as polymers of lactic acid and glycolic acid, polyanhydrides, polyurethanes, and natural polymers such as alginate and other polysaccharides including dextran and cellulose, collagen, albumin and other hydrophilic proteins, zein and other prolamines and hydrophobic proteins, copolymers and mixtures thereof.

One of skill in the art would know what peptide segments to include as protease substrates/cleavage sites in the protease activity sensors or biocomparators of the disclosure. One can use an online tool or publication to identify protease substrates/cleavage sites. For example, cleavage sites are predicted in the online database PROSPER, described in Song, 2012, PROSPER: An integrated feature-based tool for predicting protease substrate cleavage sites, *PLOSOne* 7 (11): e50300, incorporated by reference. Any of the compositions, structures, methods or activity sensors discussed herein may include, for example, any suitable cleavage site, as well as any further arbitrary polypeptide segment to obtain any desired molecular weight. To prevent off-target cleavage, one or any number of amino acids outside of the cleavage site may be in a mixture of the D and/or the L form in any quantity.

The biological sample may be any sample from a subject in which the reporter may be detected. For example, the sample may be a tissue sample (such as a blood sample, a hard tissue sample, a soft tissue sample, etc.), a urine sample, saliva sample, mucus sample, fecal sample, seminal fluid sample, or cerebrospinal fluid sample.

Pharmaceutical compositions including the disclosed protease activity sensors or bicomparators are disclosed. Pharmaceutical compositions containing protease activity sensors or bicomparator are administered by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration. The precise dosage will vary according to a variety of factors such as subject-dependent variables (e.g., age, immune system health, etc.), the disease, and the treatment being effected.

Compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more of the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic aci), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

In embodiments the compositions are formulated for oral delivery. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013,556). In general, the formulation will include the peptide (or chemically modified forms thereof) and inert ingredients which protect peptide in the stomach environment, and release of the biologically active material in the intestine.

The agents can be chemically modified so that oral delivery of the derivative is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane.

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The agent can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the drug is enclosed in a semipermeable membrane which allows water to enter and push drug out through a single small opening due to osmotic effects.

For oral formulations, the location of release may be the stomach, the small intestine (the duodenum, the jejunum, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™ cellulose acetate phthalate (CAP), Eudragit L™, Eudragit S™, and Shellac™. These coatings may be used as mixed films.

The disclosed immunotherapeutic agents can be applied topically. Topical administration does not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns. A wide range of mechanical devices designed for pulmonary delivery of therapeutic products can be used, including but not limited to nebulizers, metered dose inhalers, and powder inhalers, all of which are familiar to those skilled in the art. Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations may require the inclusion of penetration enhancers.

The biological sample may be any sample from a subject in which the reporter may be detected. For example, the sample may be a tissue sample (such as a blood sample, a hard tissue sample, a soft tissue sample, etc.), a urine sample, saliva sample, mucus sample, fecal sample, seminal fluid sample, or cerebrospinal fluid sample. In some aspects, a sample may be obtained for the tissue or bodily fluid of a subject or from a swab taken from a patient. The sample may include a fine needle aspirate, a biopsy, or a bodily fluid from the patient. The sample may be processed by, for example, to generate a suspension with an appropriate solution. Such solution will generally be a balanced salt solution, e.g. normal saline, PBS, Hank's balanced salt solution, etc., and in certain instances supplemented with fetal calf serum or other naturally occurring factors, in conjunction with an acceptable buffer at low concentration, generally from 5-25 mM. Convenient buffers include HEPES, phosphate buffers, lactate buffers, etc. In a preferred embodiment, the sample is a respiratory swab (e.g., a buccal, nasal, or throat swab). The swab may be placed into a sterile tube with a medium (e.g., Hank's balanced salt solution). The medium may also include antibiotics to reduce the possibility of bacterial contamination.

EXAMPLES

Example 1: GranzymeB/Thrombin AND-Gate Protease Activity Sensor

Figure 9:
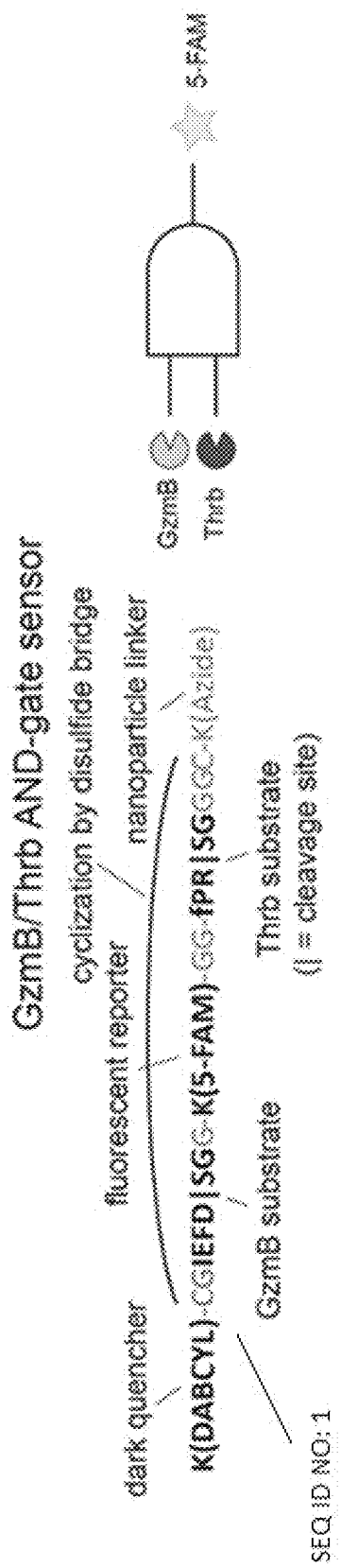
FIG. 9 shows a schematics of an exemplary protease activity sensor (SEQ ID NO: 1).

FIGS. 9-14 show AND-gate sensors that sense the proteases granzyme B (GzmB) and thrombin (Thrb), which have roles in target cell killing by the immune system and blood clotting, respectively. These AND-gate protease sensors are designed to emit fluorescent reporters (5-FAM) only after cleavage of both protease substrates (FIG. 9). FIG. 9 shows that the protease activity sensor contains a dark quencher (DABCYL), a fluorescent reporter (5-FAM), substrates for both GzmB and Thrb (bold, cleavage sites marked with "I"), and an azide for click conjugation to a scaffold, such as a nanoparticle. A disulfide bridge cyclizes the peptide to ensure quenching of 5-FAM unless both proteases are present. When the AND condition is met, i.e., a state represented by "1,1", 5-FAM fluoresces.

Figure 10:
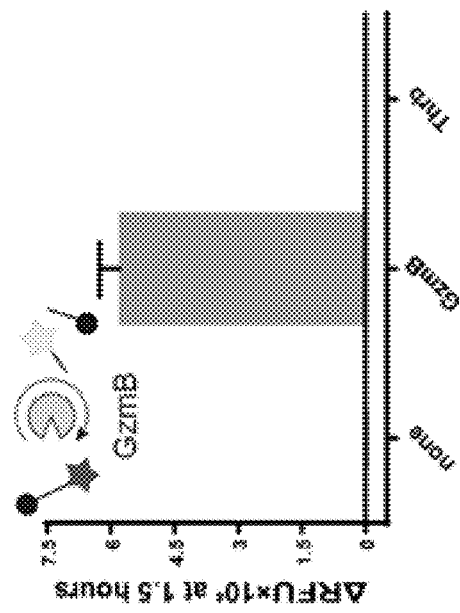
FIGS. 10-14 show experimental results for an exemplary protease activity sensor.
Figure 11:
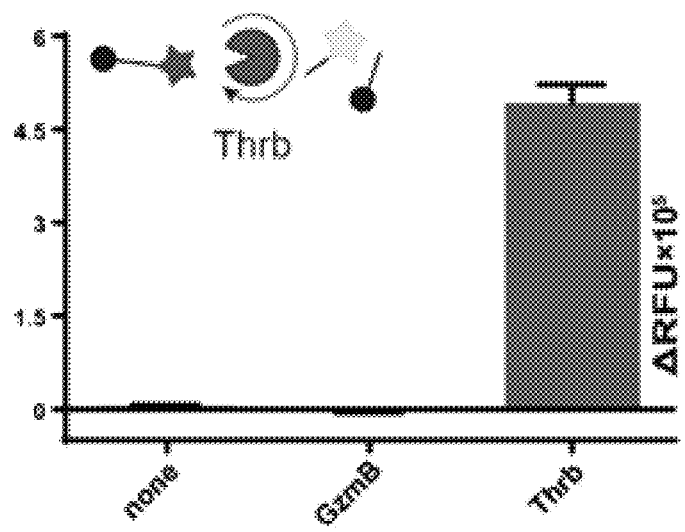

To validate sensor design, the specificity of the protease substrates were tested to ensure each substrate could be cleaved by only one of the chosen proteases. The individual protease substrates were labeled with a fluorescent quencher and dye. Cleavage assays were performed by incubating the substrates with GzmB or Thrb and monitoring fluorescence. Indeed, the GzmB substrate was cleaved effectively by GzmB alone (FIG. 10), and the Thrb substrate was cleaved only by Thrb (FIG. 11). FIGS. 10-11 show: mean change in fluorescence after incubation of nanoparticle-conjugated GzmB substrate (450 nM) and Thrb substrate (330 nM), respectively, with no protease, 275 nM GzmB, or 33 nM Thrb for 1.5 hours, n=3.

Figure 12:
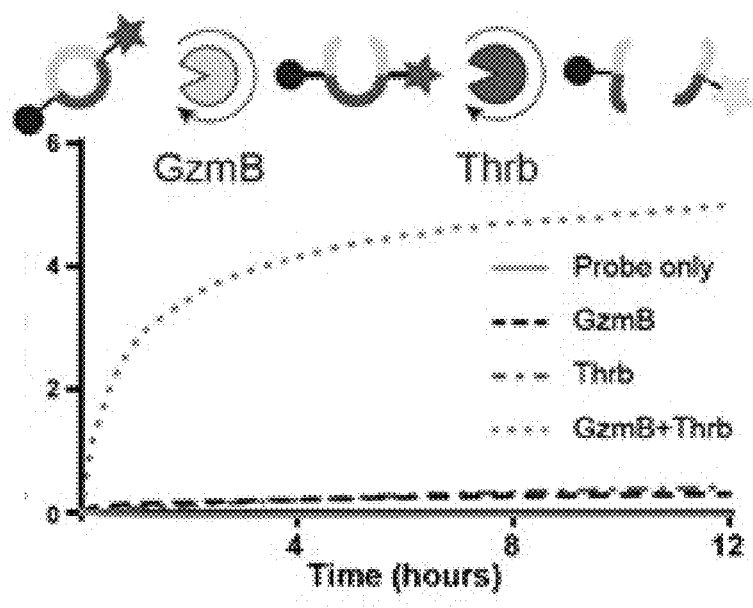

Next, the AND-gate logic protease sensor was tested in a cleavage assay. The reporter molecule emits a high fluorescent signal when both proteases are present together but not when either protease is present alone (FIG. 12). This indicates that the detectable signal was only present upon cleavage by both proteases. FIG. 12 shows: kinetic trace of mean change in fluorescence during incubation of nanoparticle-conjugated GzmB/Thrb AND-gate sensor (1 μM) with 125 nM GzmB and/or 3.7 nM Thrb for 12 hours, n=2.

Figure 13:
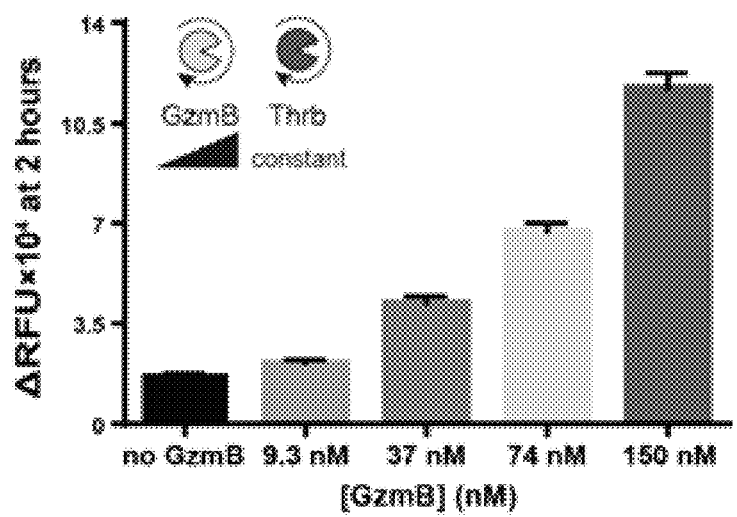
Figure 14:
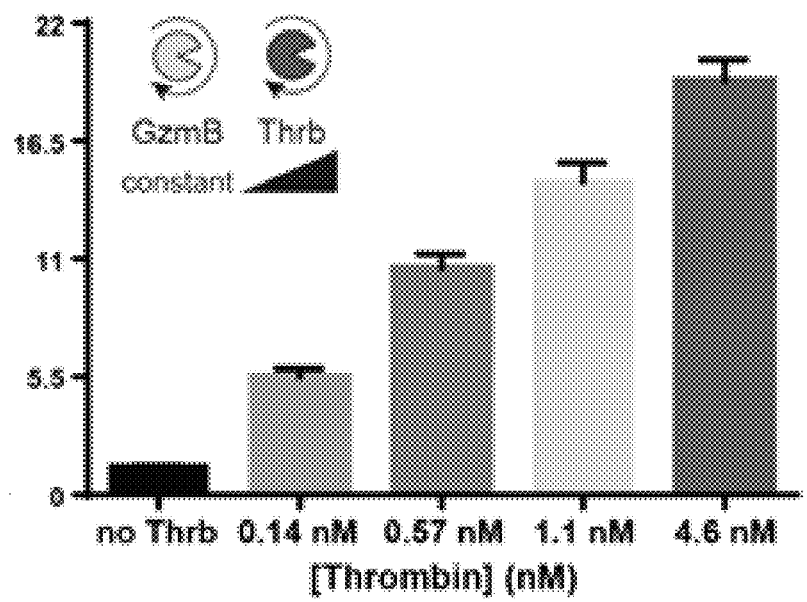

FIGS. 13-14 show that the AND-gate logic sensor is very sensitive to small changes in the concentration of both proteases even in the nanomolar range. Thus, the presence of even small amounts of a protease can be detected if the other protease is also present. FIGS. 13-14 show: mean change in fluorescence after incubation of the AND-gate sensor with (FIG. 13) 9.2 nM Thrb and varying concentrations of GzmB (0-150 nM) or (FIG. 14) 300 nM GzmB and varying concentrations of Thrb (0-4.6 nM) for 2 hours, n=2. For all fluorescent readings, samples were excited at 485 nm, emission was measured at 528 nm, and samples were incubated at 37° C.

Example 2: AND-Gate Protease Activity Sensor in a Living System

Figure 15:
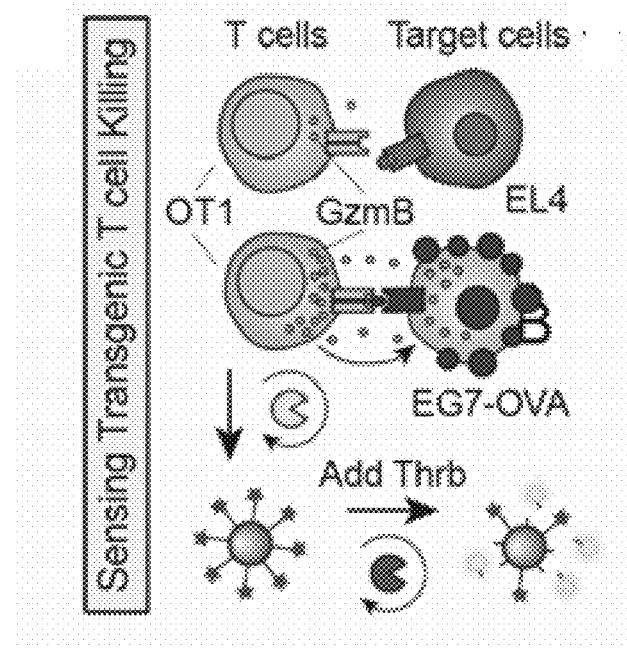
FIG. 15 shows a schematic of a protease activity sensor.
Figure 16:
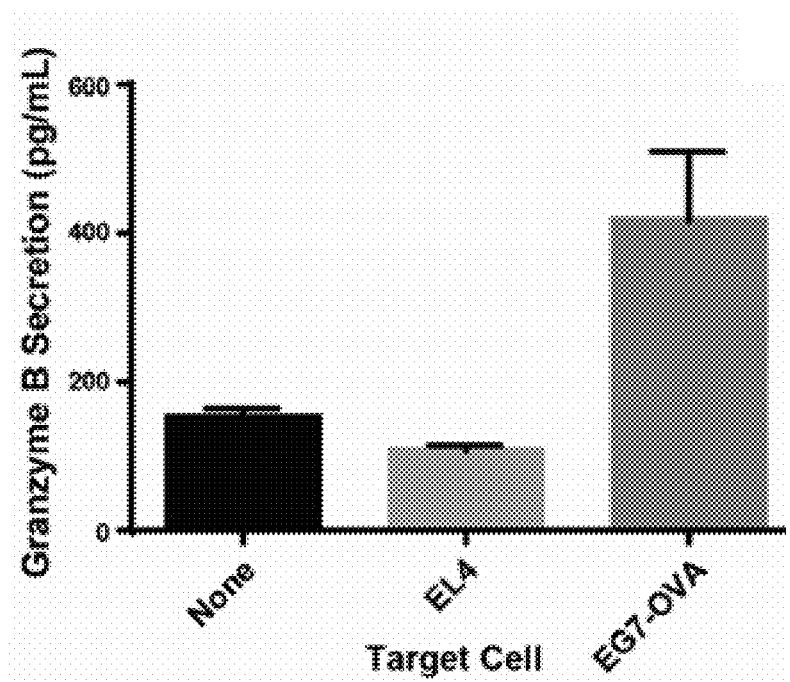
FIGS. 16-17 show experimental results for a protease activity sensor.
Figure 17:
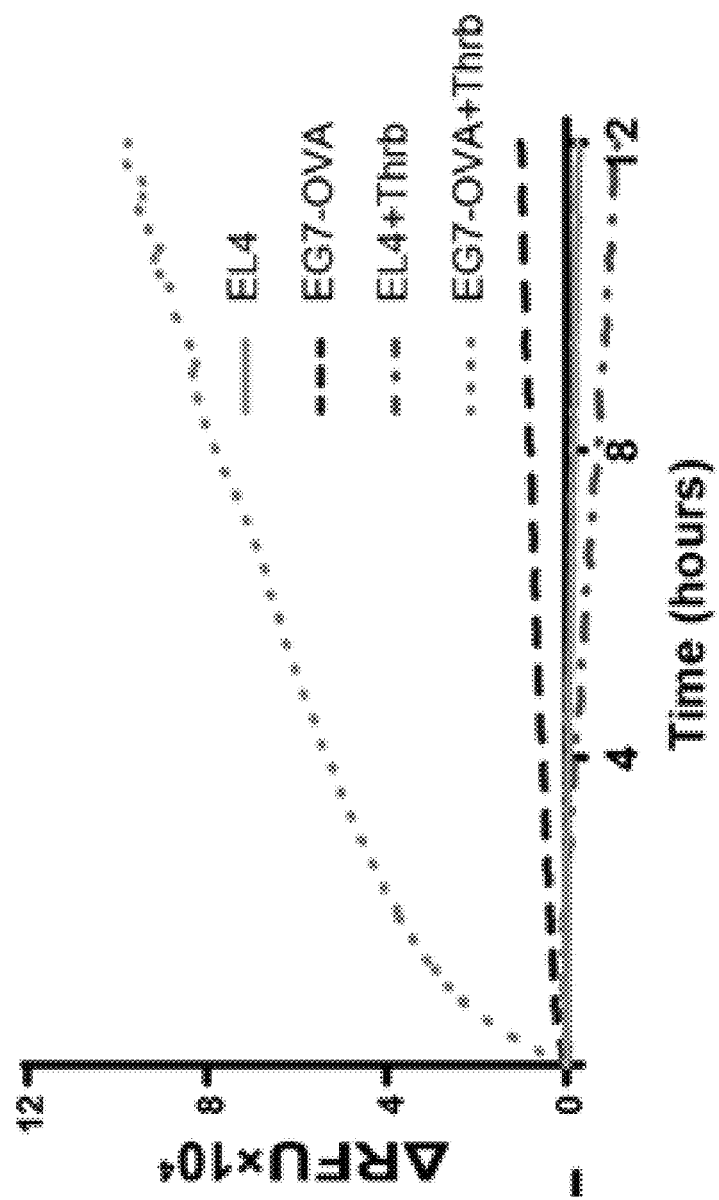

FIGS. 15-17 show an example of the disclosed AND-gate protease activity sensors used with a living system. The sensors were evaluated in an in vitro transgenic T-cell killing assay in which cytotoxic T-cells taken from OT1 mice were co-incubated with target cells EL4 and EG7-OVA (FIG. 15). OT1 T cells can recognize the OVA antigen and mount an immune response, so the T-cells would theoretically respond to the EG7-OVA cells but not to the EL4 cells. Supernatant was harvested from the co-incubation and quantified the immune response by GzmB secretion using ELISA (FIG. 16). The concentration was measured after overnight co-incubation at 37° C. with target cells, as measured by ELISA, n=3. It was confirmed that co-incubation of OT1 cells with EG7-OVA cells, but not with EL4 cells, increases GzmB secretion by OT1 cells.

Then we cleavage assays were run with the AND-gate sensors, using the supernatant as a GzmB source and adding Thrb. FIG. 17 shows the kinetic trace of mean change in fluorescence during incubation of nanoparticle-conjugated GzmB/Thrb ABD-gate protease activity sensor (1 μM) with 10% supernatant from EL4 and EG7-OVA, co-incubation and/or 3.7 Thrb for 12 hours, n=3. Data for EL4 and EG7-OVA were normalized by subtraction of trace using OT1-only supernatant, and data for EL4+Thrb and EG7-OVA+Thrb were normalized by subtraction of trace using OT1-only supernatant and Thrb. A high signal was attained only when Thrb was added to the GzmB-high OT1/EG7-OVA supernatant, demonstrating the AND-gate protease activity sensor can accurately probe biological activity based on Boolean logic.

Example 3: AND-Gate Protease Activity Sensor to Monitor Efficacy and Response to Therapeutic Treatment FIGS. 18-21 show AND-gated protease sensors to monitor the efficacy and response to therapeutic treatment. Cancer immunotherapies are limited by their off-target effects, so noninvasively detecting intratumoral immune activity would substantially improve treatment monitoring. In addition, solely monitoring immune activity in a patient would not confirm immunotherapy efficacy because the immune system could be activated against other pathologies (e.g. viral infections). Thus, the AND-gate logic sensor could improve the specificity of treatment monitoring by sensing for both GzmB and a tumor-associated protease. Matrix metalloproteinases (MMPs) are a class of proteases that are highly upregulated in many types of cancer because of their role in extracellular matrix remodeling, which helps tumors grow, invade, and metastasize.

Figure 18:
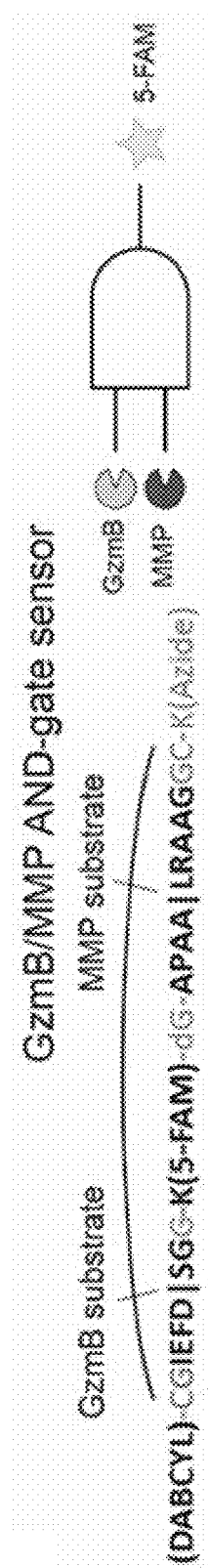
FIG. 18 shows a schematic of a protease activity sensor (SEQ ID NO: 2).
Figure 19:
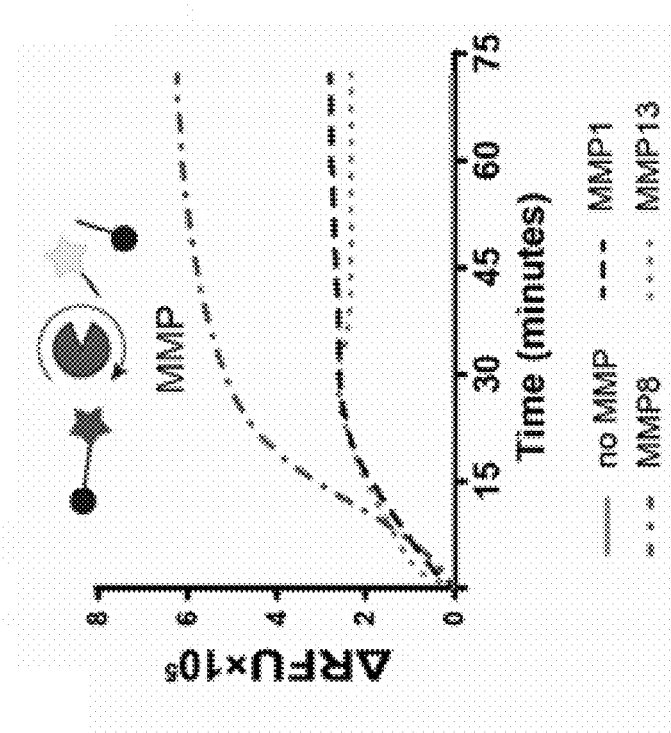
FIGS. 19-21 show experimental results for a protease activity sensor.

FIG. 18 shows the AND-gate protease activity sensor that probes both GzmB and MMPs. The MMP substrate was designed based upon literature, and was tested to ensure the substrate could be cleaved by different pure MMPs (FIG. 19). FIG. 19 shows a kinetic trace of mean change in fluorescence during incubation of MMP substrate (5 μM) with 100 nM different MMPs for 75 minutes, n=2. The substrate was cleaved with high activity by MMP1, MMP8, and MMP13.

Figure 20:
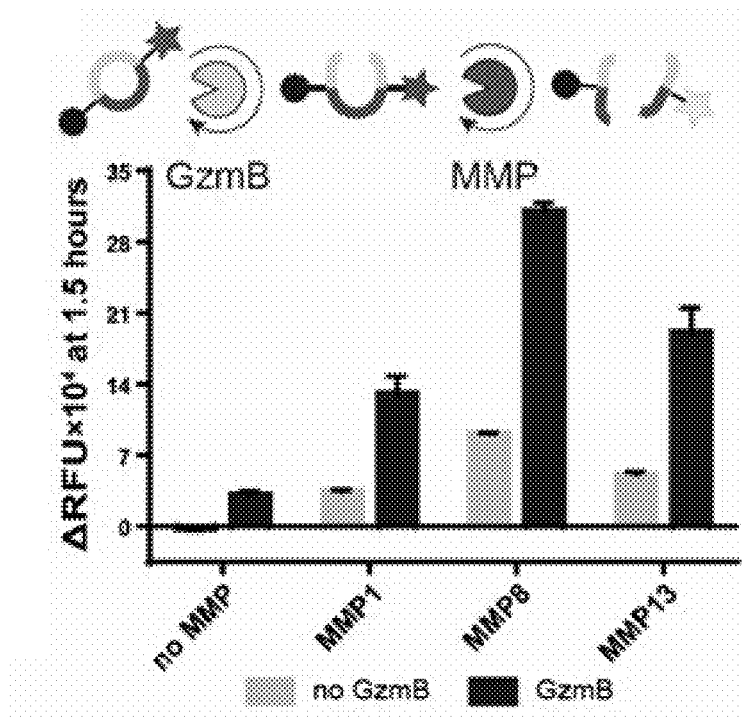

Then a cleavage assay was performed with the GzmB/MMP AND-gate sensor, testing the probe with each MMP with and without GzmB (FIG. 20). The addition of GzmB to all three MMPs drastically increased the fluorescent signal by over two-fold, verifying that this probe follows the desired Boolean logic.

Figure 21:
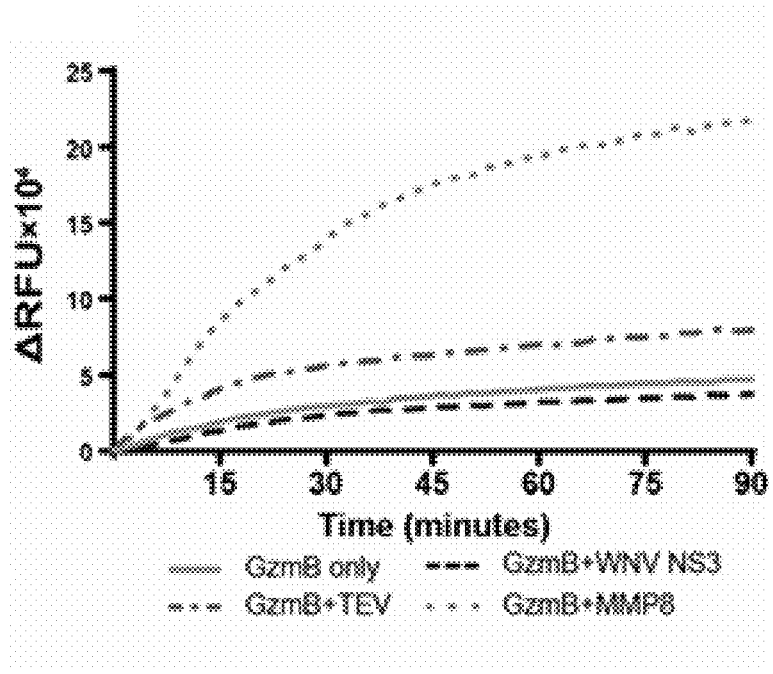

Next the protease activity sensor was incubated with GzmB and either MMP8 or one of two viral proteases (West Nile Virus NS3 protease and Tobacco Etch Virus protease) to show the AND-gate sensor can distinguish immune activity in tumors from viral infections (FIG. 21). The sensor produced low signals with the viral proteases compared to MMP8.

FIGS. 20-21 show mean change in fluorescence (7D, kinetic trace) after incubation of GzmB/MMP AND-gate sensor (5 µM) with (7C) 300 nM GzmB and/or 100 nM different MMP's or (7D) 300 nM GzmB and 100 nM West Nile Virus NS3 protease, Tobacco Etch Virus protease, or MMP8 for 1.5 hours, n=3.

Example 4: Exemplary AND-Gate Biocomparator

Figure 22:
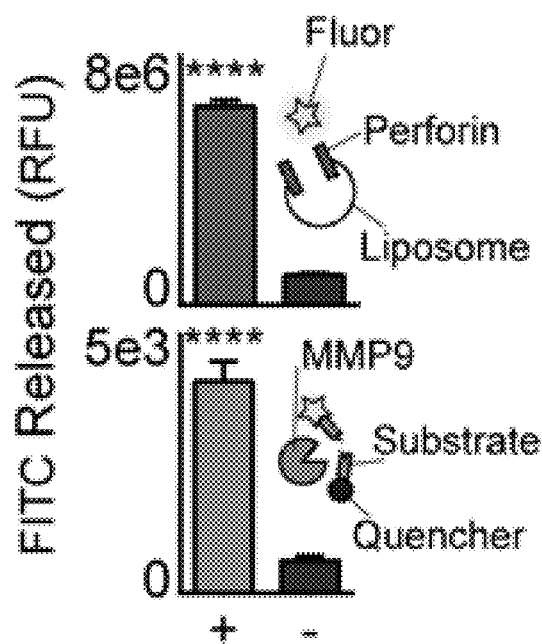
FIG. 22-23 show experimental results related to a biocomparator.

The concept of an AND-gate logic sensor to systems are not limited to implementations with protease activity sensors. The disclosure provide an AND-gate biocomparator consisting of a liposome in a peptide cage, such as that formed by MMP substrates. The liposome encased a fluorescent reporter, so the peptide cage would have to be cleaved and the liposome would have to be perforated by perforin, a cytolytic protein used by T-cells, for the reporter to be released. Results show that perforin can perforate the liposome by placing a fluorescent reporter in the liposome, which was released upon perforation (FIG. 22). Results also confirmed MMP9 can cleave the MMP substrate by cleavage assay (FIG. 22). FIG. 22 shows a fluorescent assay for detecting the opening of bare liposomes with perforin (top) and cleavage of the peptide substrate with protease MMP9 (bottom).

Figure 23:
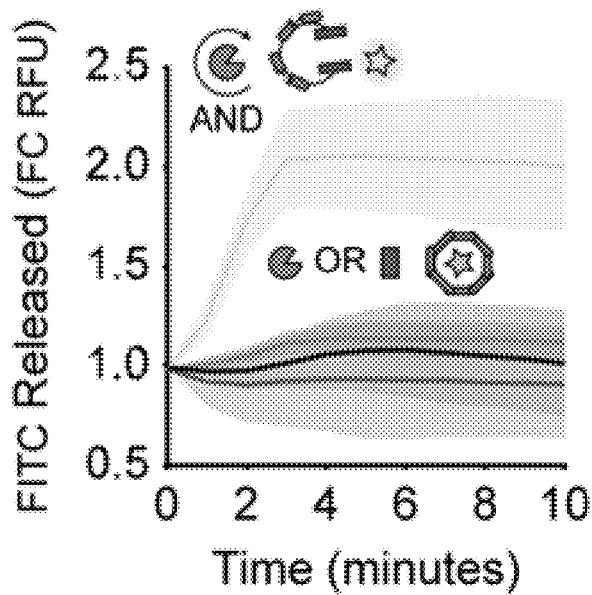
Figure 24:
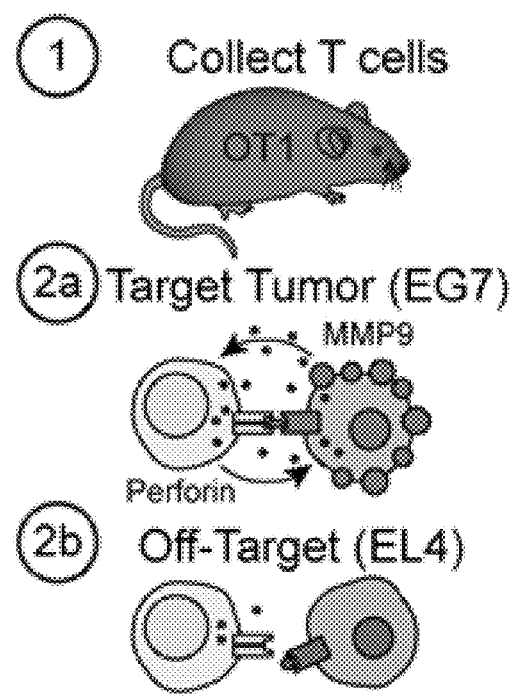
FIG. 24 shows a schematic of an experimental protocol using a biocomparator.
Figure 25:
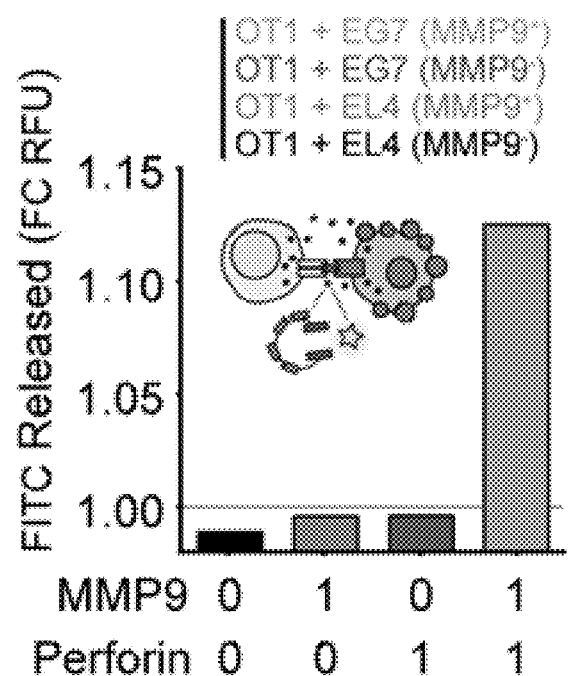
FIG. 25 shows a schematic of a biocomparator and experimental results.

Next, the peptide-caged biocomparator was tested with perforin, MMP9, or both proteins (FIG. 23). Only both proteins produced a high signal, suggesting both are necessary to release the reporter in the biocomparator. FIG. 23 shows the fluorescent assay measuring an increase in the signal from biocomparator opened by both signal protease (MMP9) and perforin. Finally, results via a T-cell killing assay showed that the biocomparator can only be opened when there is an immune response and MMP9 is present. FIG. 24 shows an experimental schematic depicting the generation of MMP9 and perforin in the context of antigen specific killing. T-cells were harvested from OT1 mice and co-incubated with target tumor cells (EG7), which secrete MMP9, as well as off-target cells. FIG. 25 shows a T-cell killing assay measuring increase in signal from bio-circuit capable of detecting both T-cell killing and tumor activity.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

What is claimed is:

1. A noninvasive method for determining protease activity in a biological sample from a subject, comprising:
   contacting the biological sample with a protease activity sensor comprising a first protease substrate and a second protease substrate, wherein the first and second protease substrates comprise protease cleavage sites,
   wherein the first substrate is cleaved by a first protease and the second substrate is cleaved by a second protease wherein the first protease and the second protease are different proteases, and
   wherein the protease activity sensor provides a detectable signal via a reporter molecule only when both the first protease substrate and the second protease substrate are cleaved;
wherein the reporter molecule is released by the protease cleavage and diffuses into circulation and into tissues that can be obtained noninvasively,
   detecting the presence of the detectable signal in a noninvasively obtained sample; and
   identifying the activity of the first protease and second protease based on the presence of the detectable signal in the sample, wherein the first and second proteases comprise granzyme B (GzmB), thrombin (Thrb), a metalloproteinase, or a viral protease;
   wherein the protease activity sensor comprises SEQ ID NO: 1 or SEQ ID NO: 2.

2. The method of claim 1, wherein the protease activity sensor is conjugated to the reporter molecule that provides the detectable signal.

3. The method of claim 2 wherein the reporter molecule is a fluorescent molecule.

4. The method of claim 3, wherein the first substrate and the second substrate are conjugated to a fluorescent quencher and cleavage of the first substrate and the second substrate permits the fluorescent molecule to provide a detectable signal.

5. The method of claim 1, wherein the protease activity sensor is a cyclic peptide.

6. The method of claim 1, wherein the protease activity sensor is bound to a scaffold.

7. The method of claim 6, wherein the scaffold is a nanoparticle.

8. The method of claim 7, wherein a plurality of protease activity sensors are bound to the nano particle.

9. The method of claim 1, wherein identifying the activity of the first protease and the second protease in the biological sample indicates a protease dysregulation.

10. The method of claim 9, wherein the protease dysregulation indicates the presence of a diseased state in the biological sample.

11. The method of claim 10, wherein the diseased state is cancer, fibrosis, a hematological disorder, an immune disorder, a viral infection, or a bacterial infection.

12. The method of claim 1, wherein the activity of the first protease and/or the activity of the second protease are promoted by a therapeutic agent.

13. A protease activity sensor comprising SEQ ID NO: 1 or SEQ ID NO: 2.

* * * * *